(12) United States Patent
Levinson et al.

(10) Patent No.: US 7,150,756 B2
(45) Date of Patent: *Dec. 19, 2006

(54) RADIOPAQUE LOCKING FRAME, FILTER AND FLEXIBLE END

(75) Inventors: Melvin E. Levinson, Miami, FL (US);
George I. Golik, Miami, FL (US);
Todd A. Hall, Goshen, KY (US);
Raymond Diaz, Weston, FL (US)

(73) Assignee: Scion Cardio-Vascular, Inc, Miami, FL (US)

(*) Notice: Subject to any disclaimer, the term of this patent is extended or adjusted under 35 U.S.C. 154(b) by 573 days.

This patent is subject to a terminal disclaimer.

(21) Appl. No.: 10/346,729

(22) Filed: Jan. 17, 2003

(65) Prior Publication Data

US 2003/0139764 A1 Jul. 24, 2003

Related U.S. Application Data

(63) Continuation-in-part of application No. 09/875,342, filed on Jun. 6, 2001, now Pat. No. 6,537,296, which is a continuation-in-part of application No. 09/660,380, filed on Sep. 12, 2000, now Pat. No. 6,344,049, which is a continuation of application No. 09/376,120, filed on Aug. 17, 1999, now Pat. No. 6,277,138.

(60) Provisional application No. 60/127,438, filed on Apr. 1, 1999.

(51) Int. Cl.
*A61M 29/00* (2006.01)
*A61B 17/22* (2006.01)

(52) U.S. Cl. ...................... 606/200; 606/159

(58) Field of Classification Search ............... None
See application file for complete search history.

(56) References Cited

U.S. PATENT DOCUMENTS

| | | | |
|---|---|---|---|
| 4,619,246 A | 10/1986 | Molgaard-Nielsen et al. | |
| 4,723,549 A | 2/1988 | Wholey et al. | |
| 5,053,008 A | 10/1991 | Bajaj | 604/104 |
| 5,108,419 A | 4/1992 | Reger et al. | 606/200 |
| 5,190,555 A | 3/1993 | Wetter et al. | 606/114 |
| 5,192,286 A | 3/1993 | Phan et al. | 606/127 |
| 5,329,942 A | 7/1994 | Gunther | 128/898 |
| 5,549,626 A | 8/1996 | Miller et al. | 606/200 |
| 5,695,519 A | 12/1997 | Summers et al. | 606/200 |
| 5,769,816 A | 6/1998 | Barbut et al. | 604/96 |
| 5,810,874 A | 9/1998 | Lefebvre | 606/200 |
| 5,814,064 A | 9/1998 | Daniel et al. | 606/200 |

(Continued)

FOREIGN PATENT DOCUMENTS

WO    WO 96/01591    1/1996

*Primary Examiner*—Glenn K. Dawson
(74) *Attorney, Agent, or Firm*—Robert C. Kain, Jr.; Fleit Kain

(57) ABSTRACT

The radially expandable frame utilized during catheterization includes a guide wire, a radiopaque radially expandable frame with distal and proximal frame ends wherein the guide wire freely passes through the proximal frame end, an elongated actuation sleeve having a flexible distal end piece (coil strain relief) through which freely passes the guide wire, and a friction locking mechanism located at the proximal end of the system which is defined by the proximal ends of the actuation sleeve and guide wire. The expandable frame includes radiopaque frame struts and has a closed, radially compact form and an open, radially expanded form. The actuator flexible end piece is a coil which enables the system to flex in excess of 90 degrees. The actuator sleeve, at its proximal end, includes a friction locking mechanism having locking members with respective locking surfaces.

11 Claims, 16 Drawing Sheets

U.S. PATENT DOCUMENTS

| | | | | |
|---|---|---|---|---|
| 5,827,324 A | | 10/1998 | Cassell et al. | 606/200 |
| 5,911,734 A | * | 6/1999 | Tsugita et al. | 606/200 |
| 5,928,260 A | * | 7/1999 | Chin et al. | 606/200 |
| 5,941,896 A | | 8/1999 | Kerr | 606/200 |
| 5,980,555 A | | 11/1999 | Barbut et al. | 606/200 |
| 6,001,118 A | | 12/1999 | Daniel et al. | 606/200 |
| 6,053,932 A | | 4/2000 | Daniel et al. | 606/200 |
| 6,059,814 A | | 5/2000 | Ladd | 606/200 |
| 6,277,138 B1 | * | 8/2001 | Levinson et al. | 606/200 |
| 6,344,049 B1 | * | 2/2002 | Levinson et al. | 606/200 |
| 6,371,971 B1 | * | 4/2002 | Tsugita et al. | 606/200 |
| 6,485,457 B1 | | 11/2002 | Hisamatsu | 604/102.02 |
| 6,485,501 B1 | | 11/2002 | Green | 606/200 |
| 6,544,279 B1 | * | 4/2003 | Hopkins et al. | 606/200 |
| 6,605,102 B1 | * | 8/2003 | Mazzocchi et al. | 606/200 |
| 6,656,203 B1 | * | 12/2003 | Roth et al. | 606/200 |
| 6,743,247 B1 | * | 6/2004 | Levinson et al. | 606/200 |
| 2002/0188314 A1 | * | 12/2002 | Anderson et al. | 606/200 |

* cited by examiner

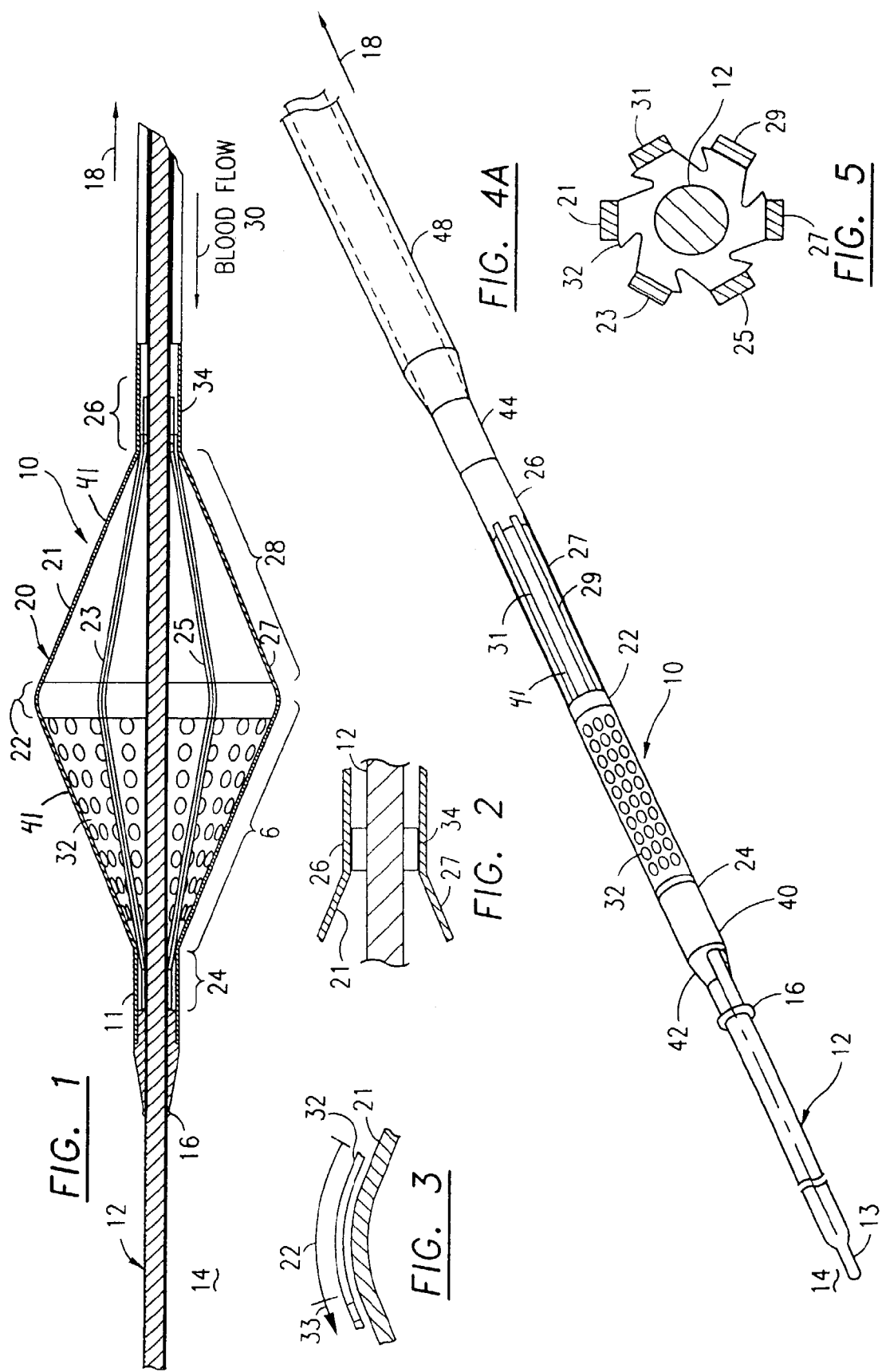

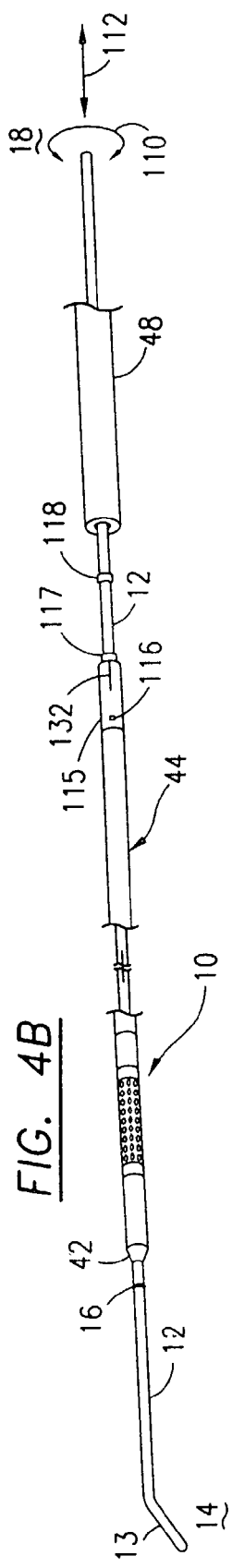
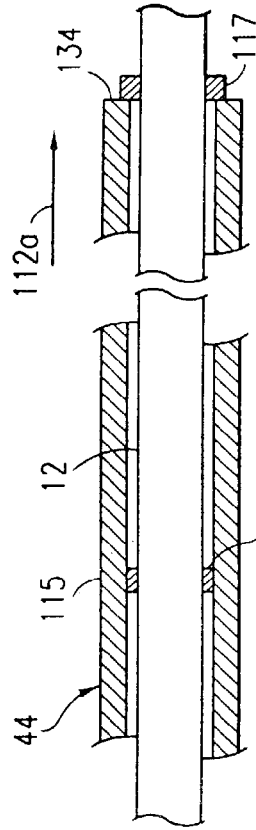
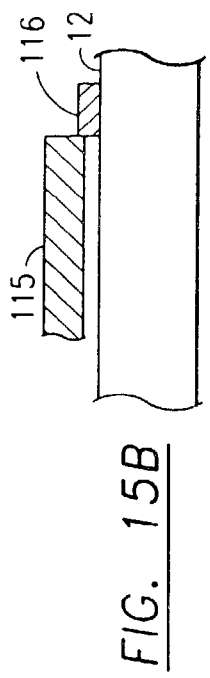
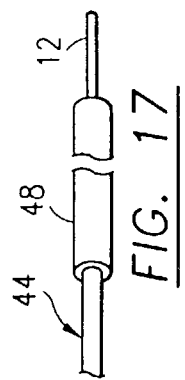
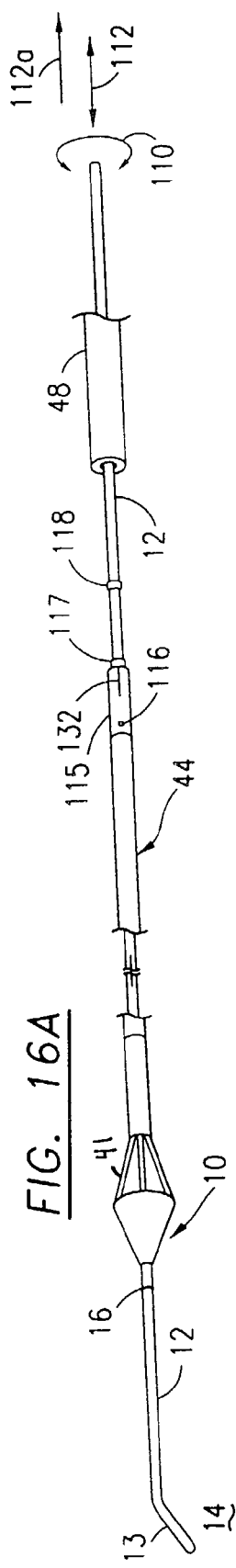

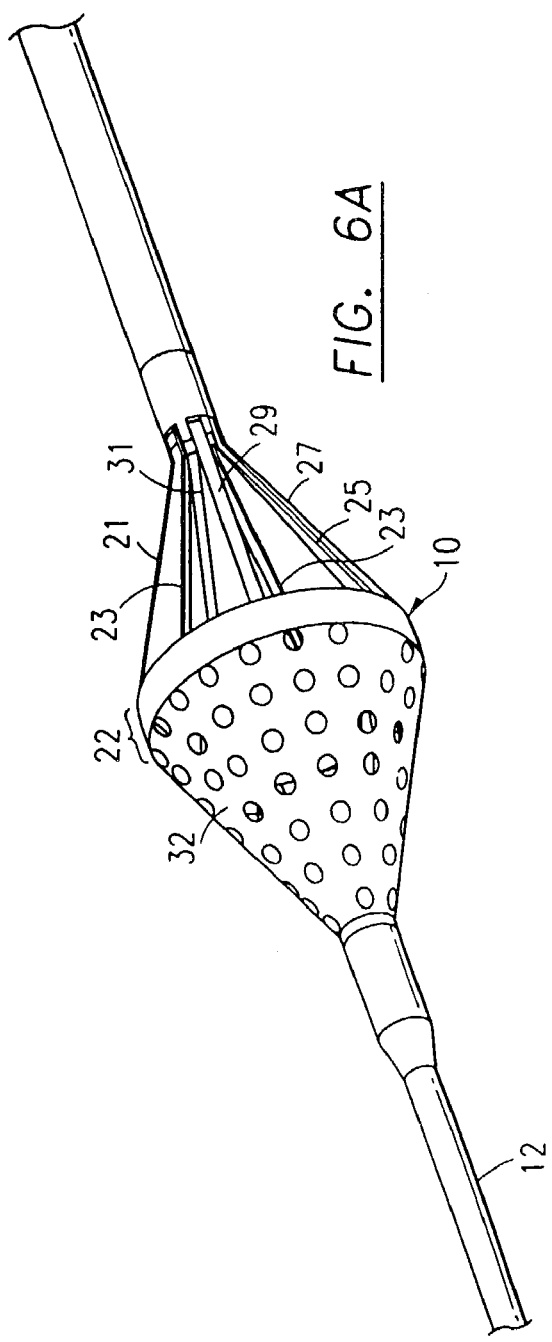
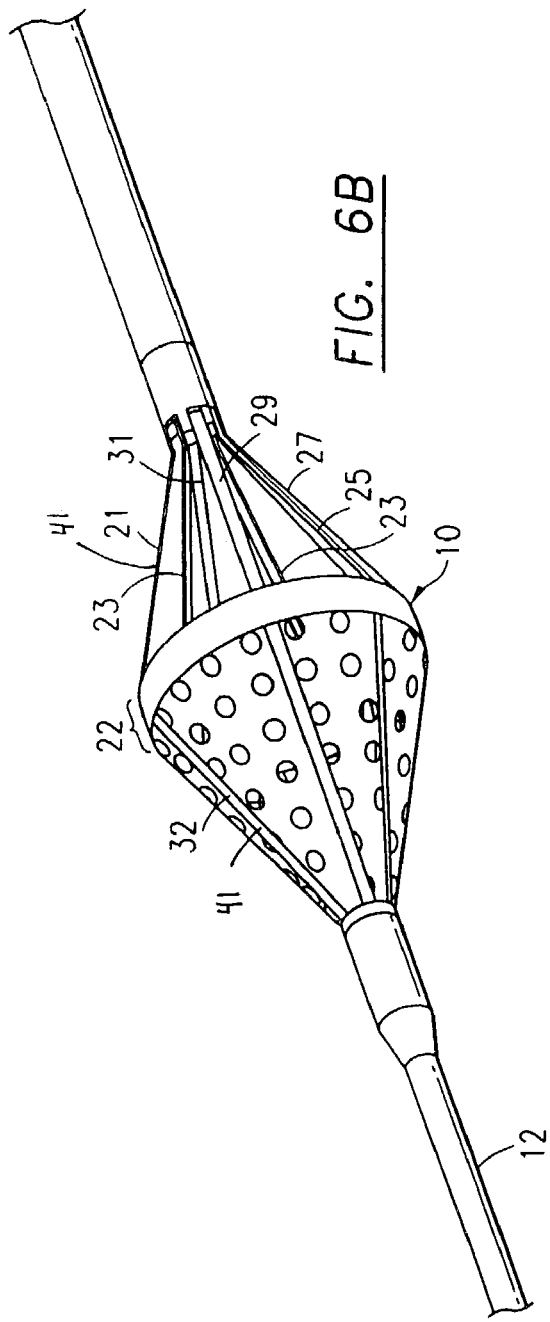

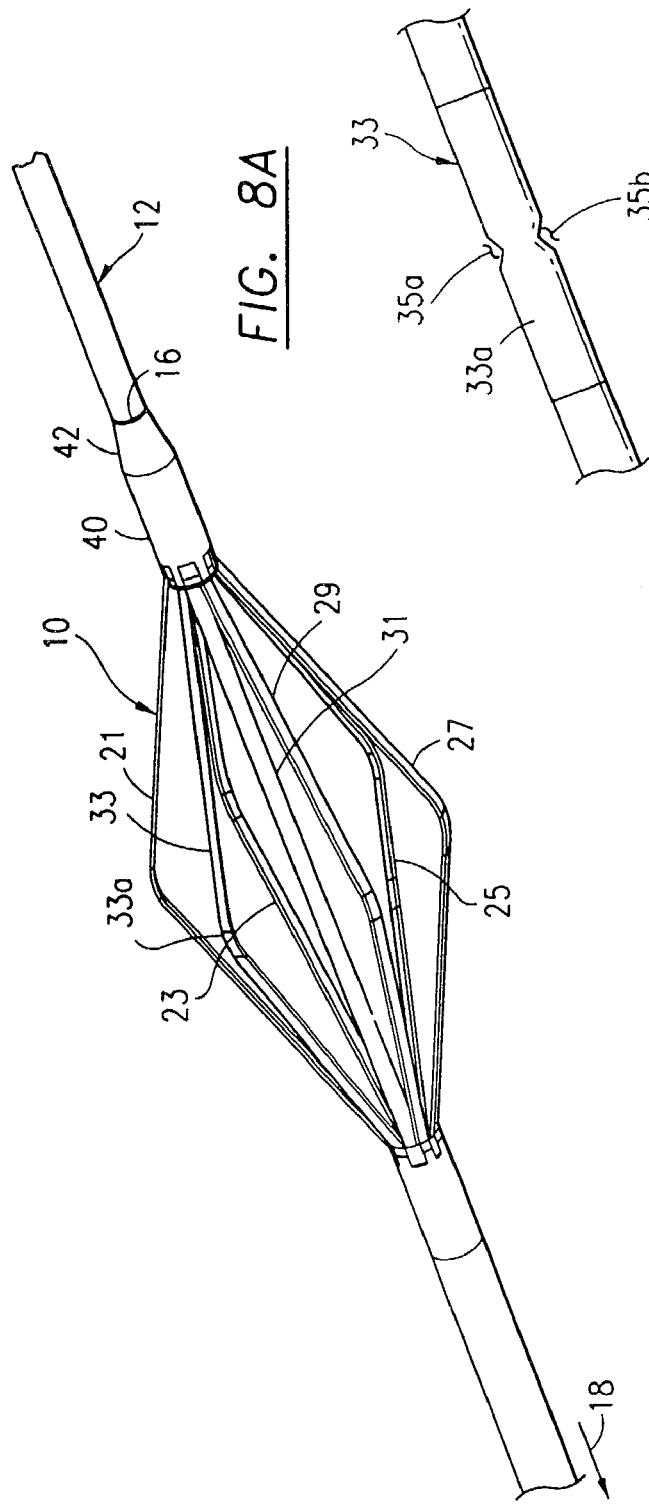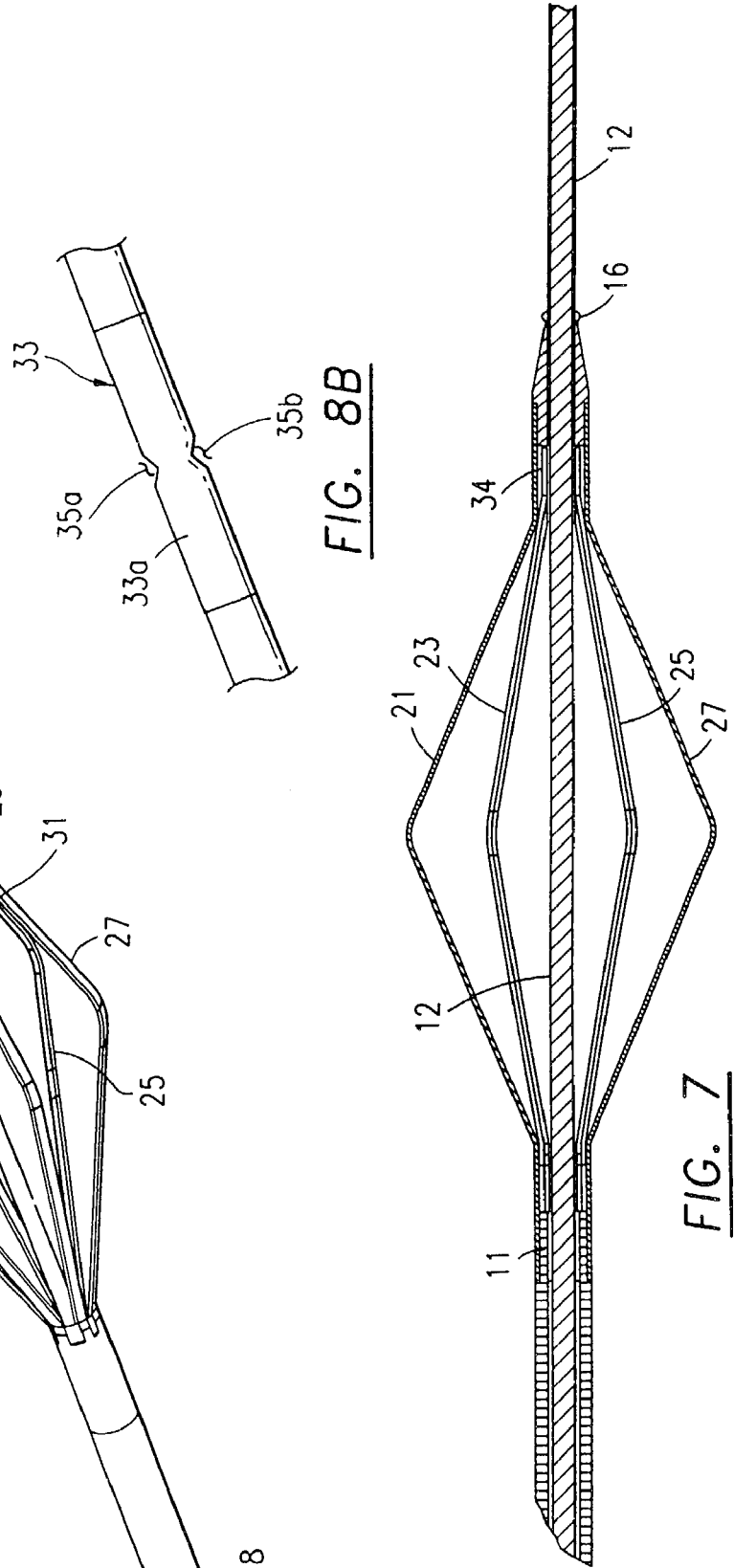

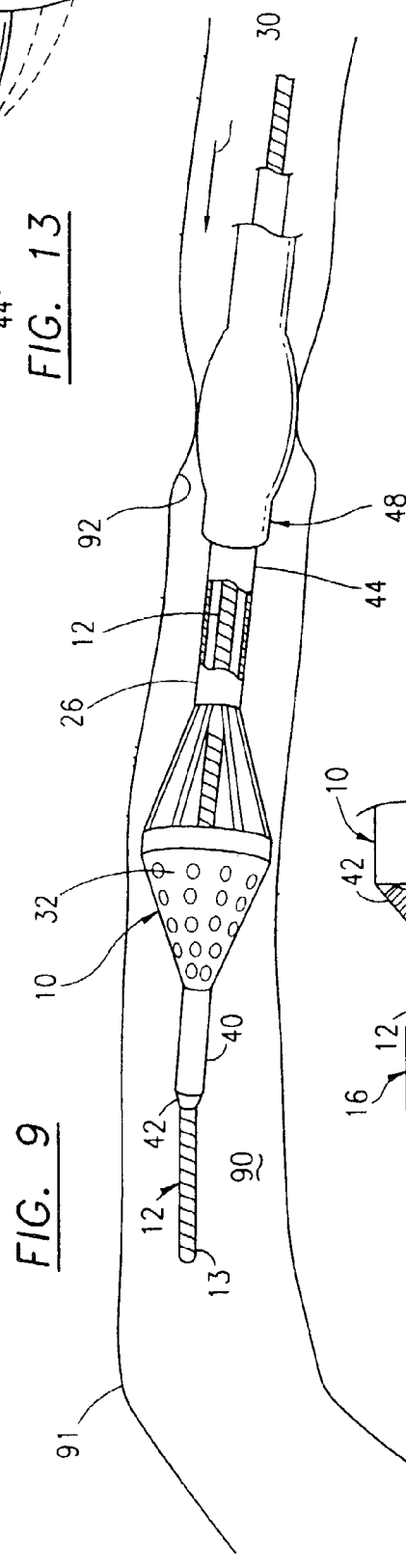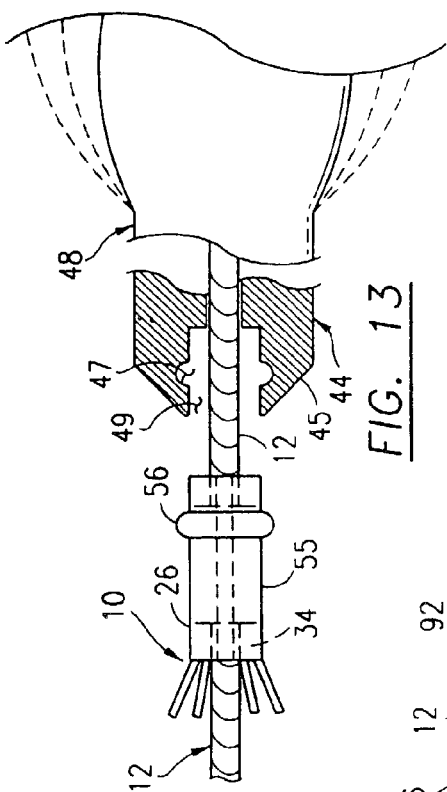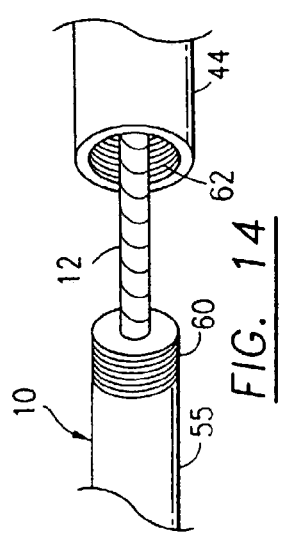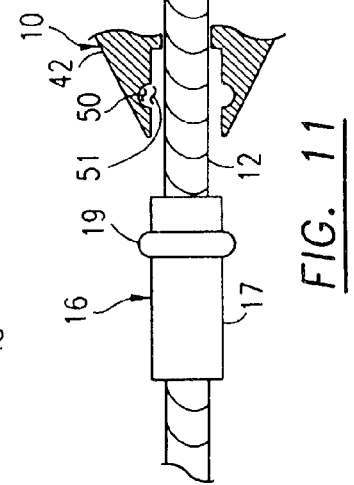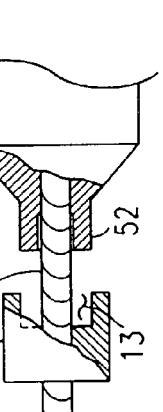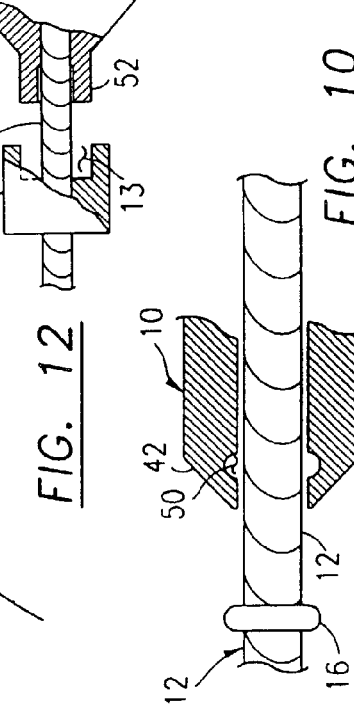

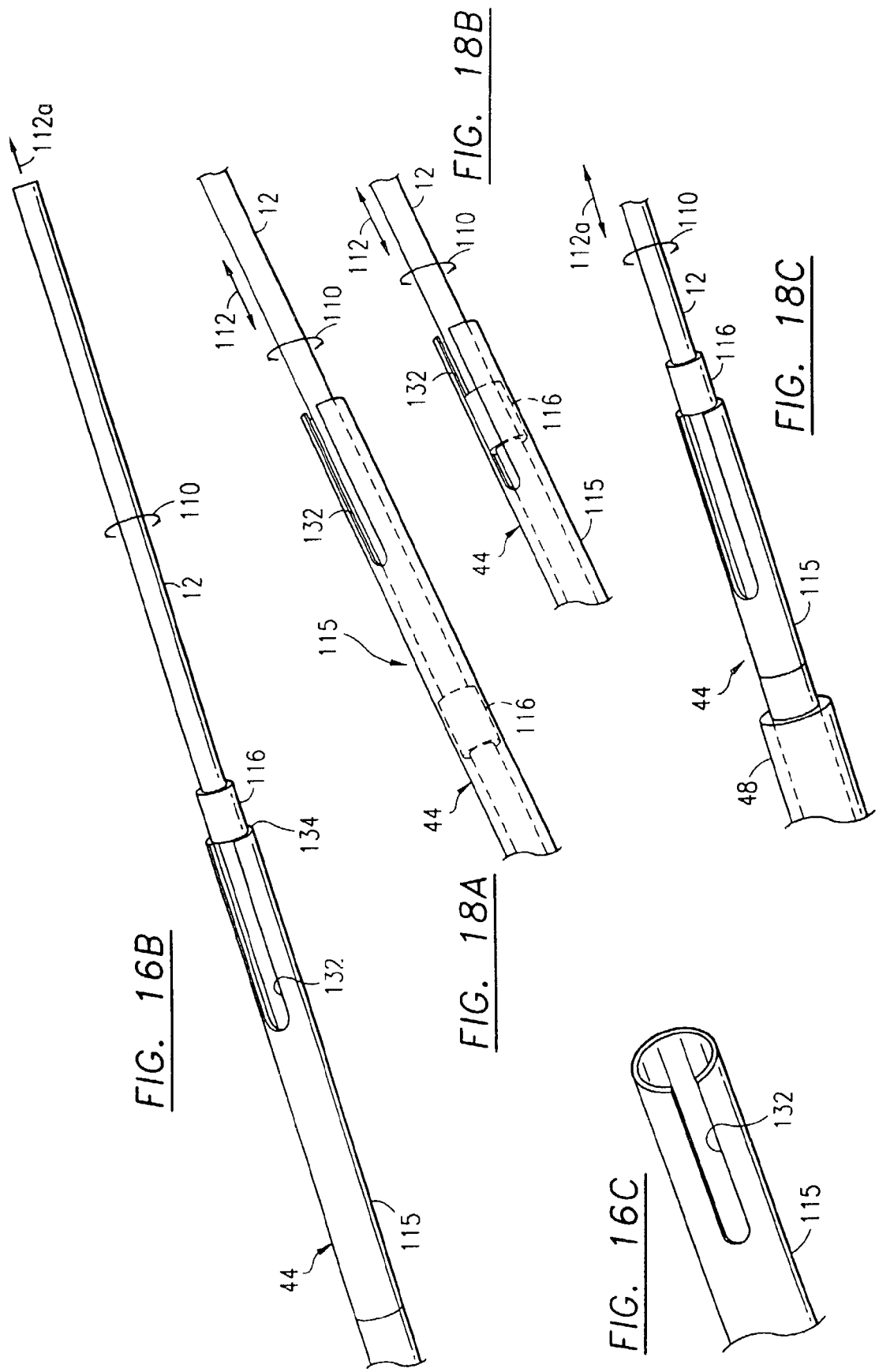

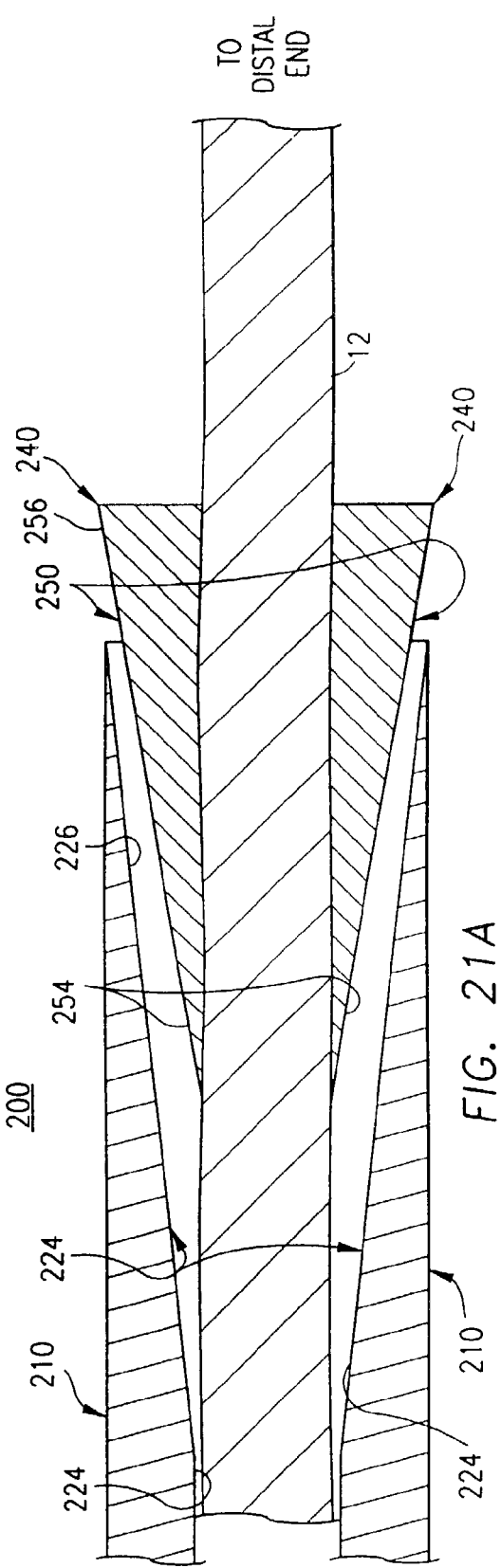
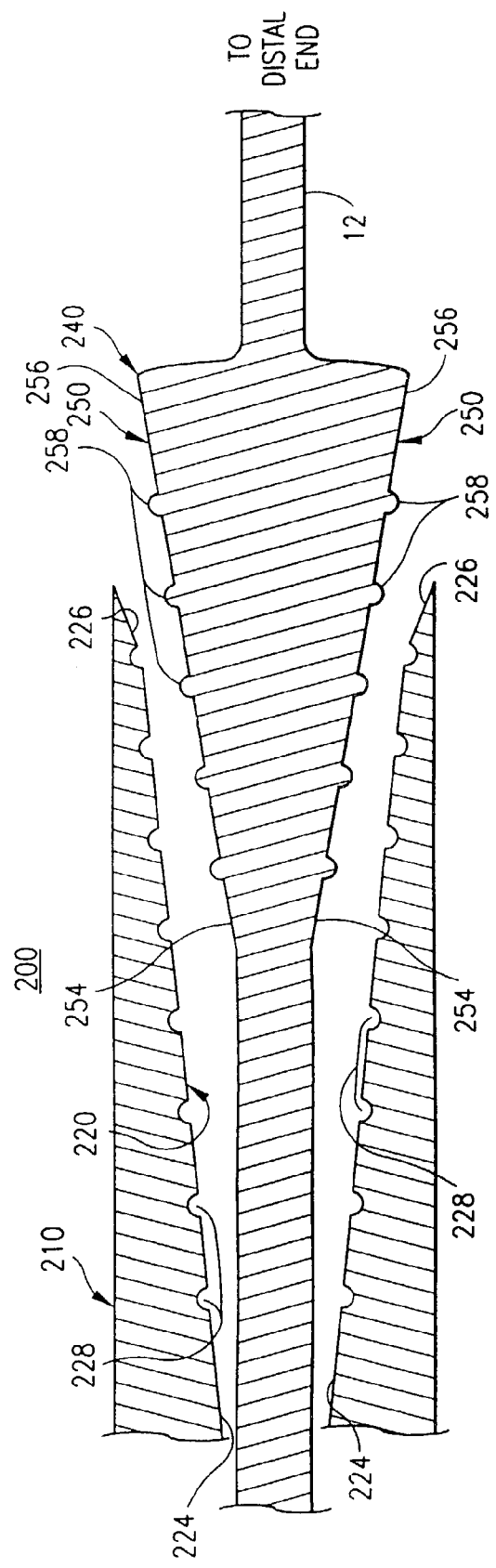
FIG. 21A
FIG. 21B

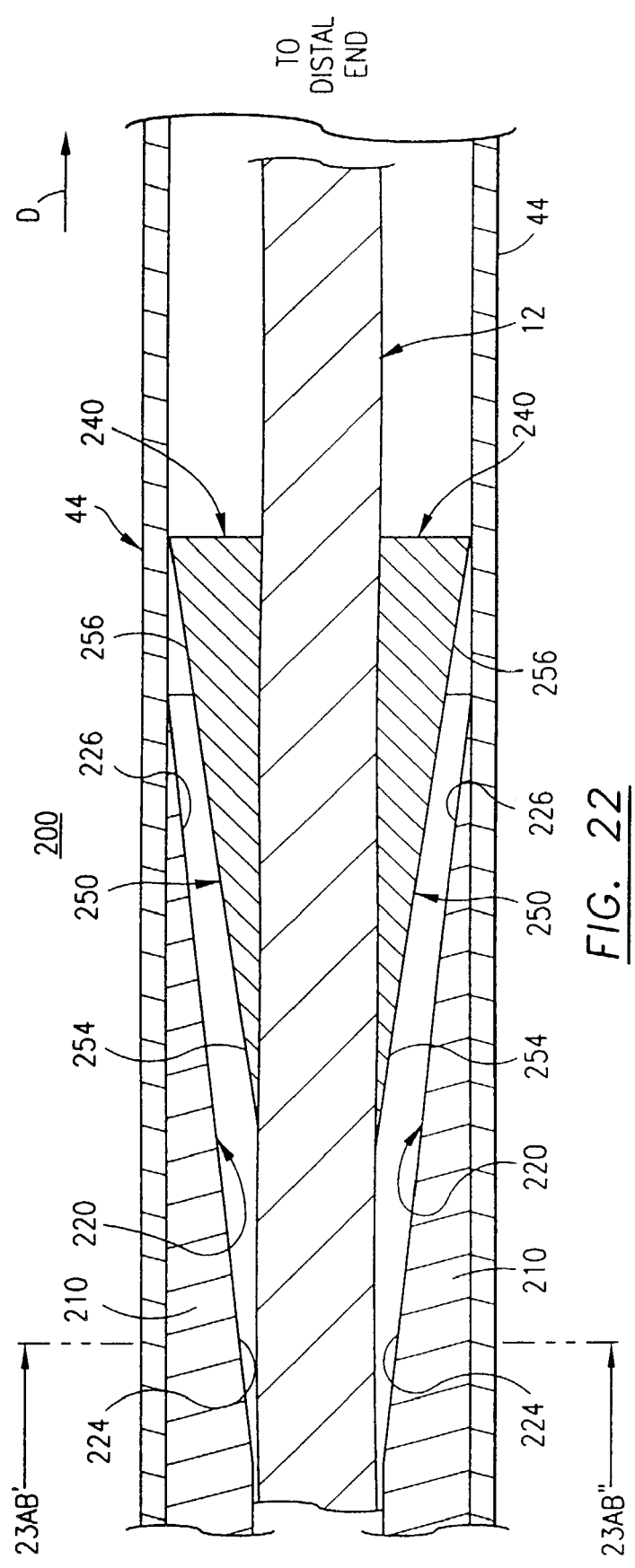
FIG. 22
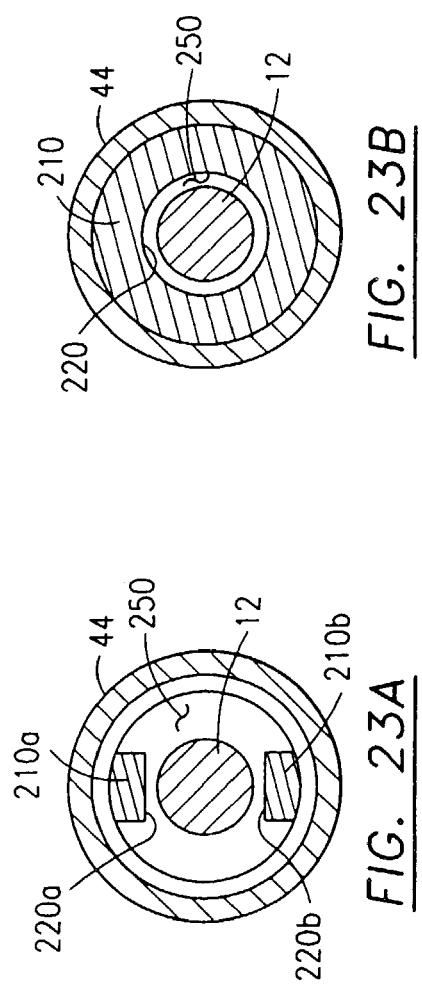
FIG. 23B
FIG. 23A

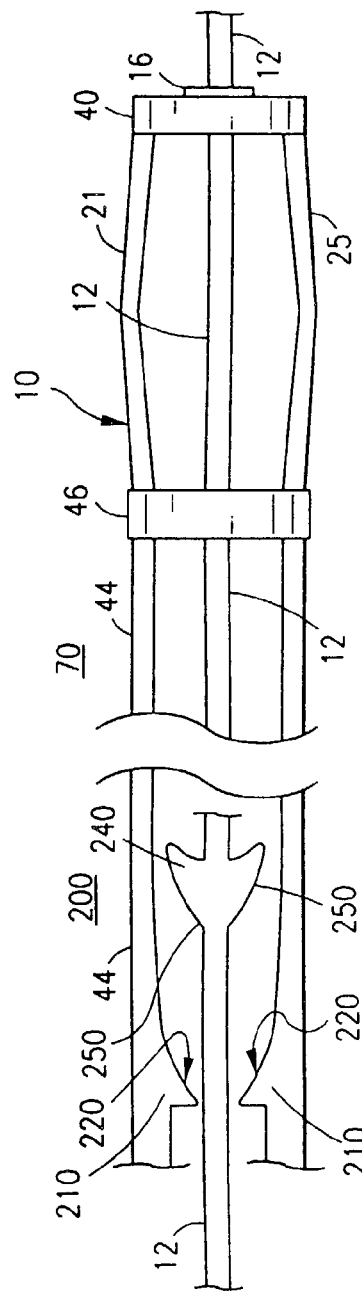
FIG. 25A
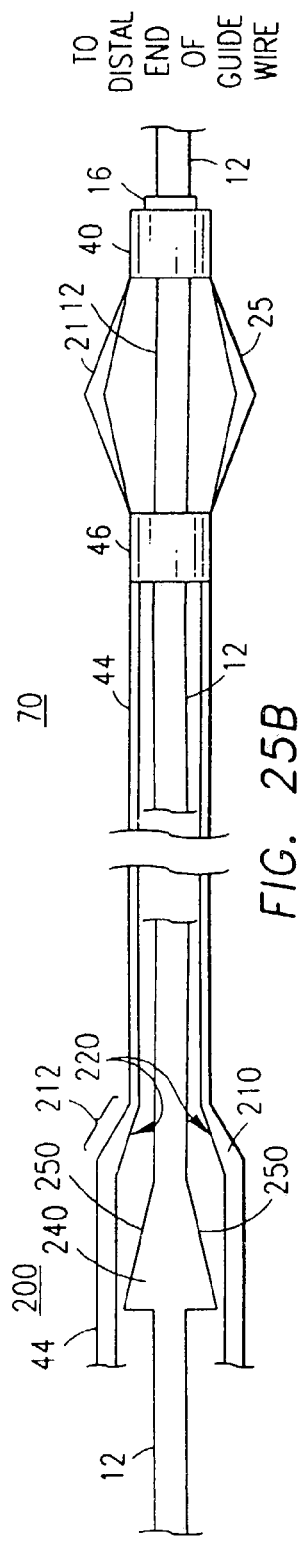
FIG. 25B
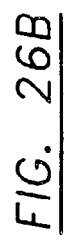
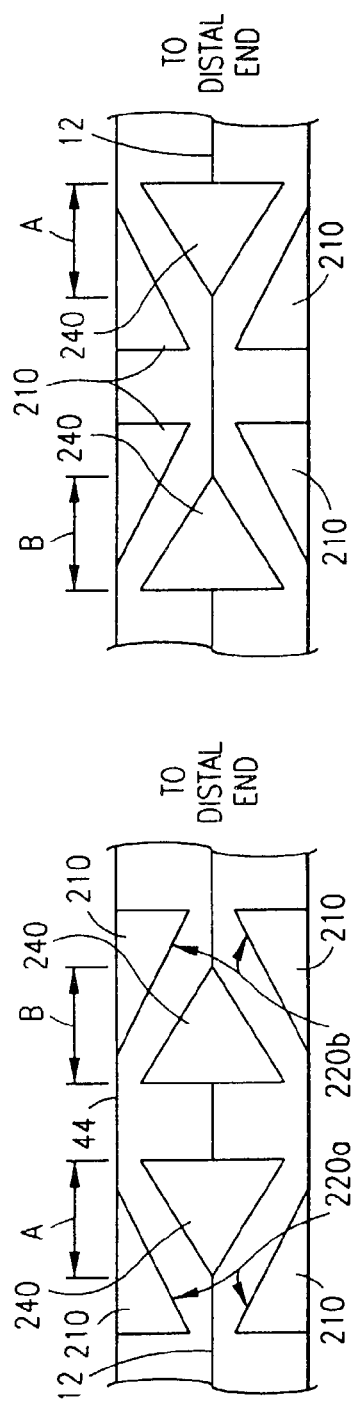
FIG. 26B
FIG. 26A

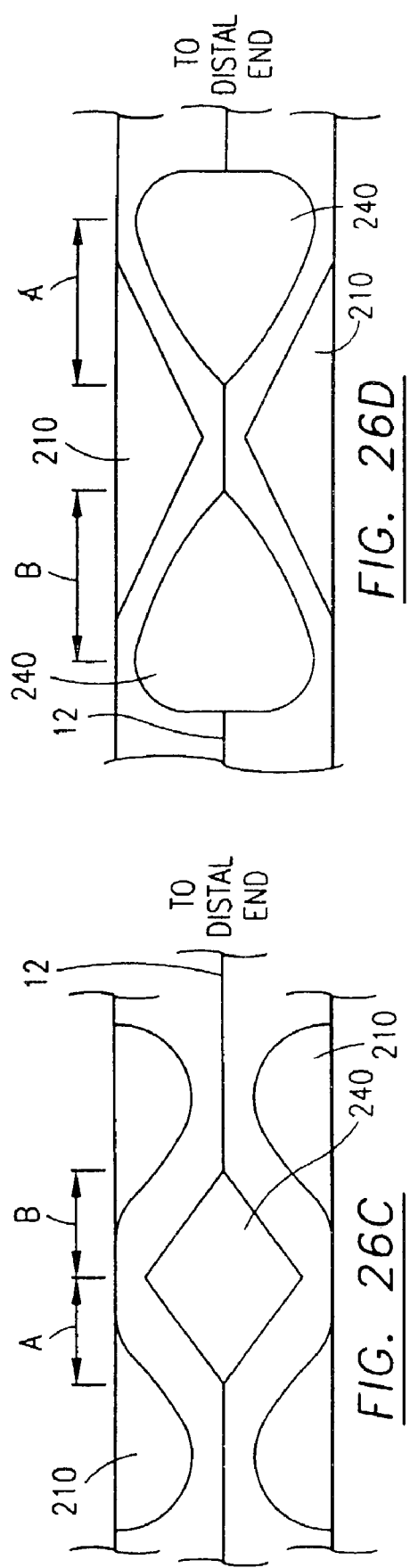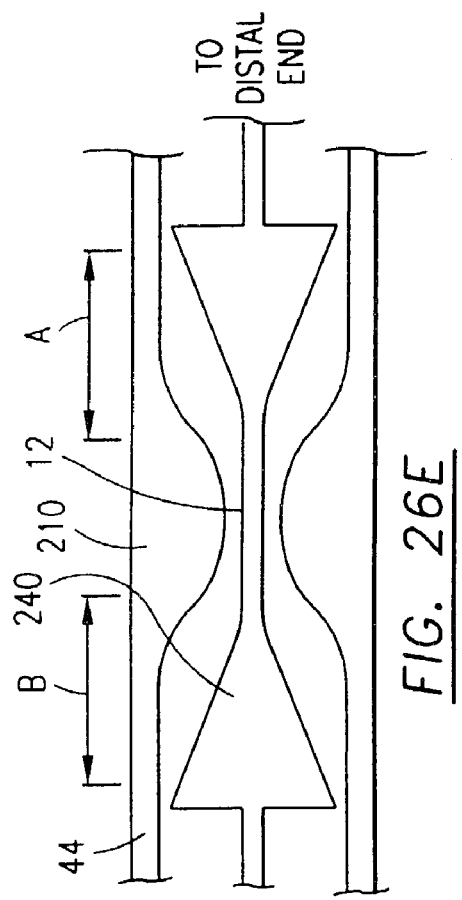

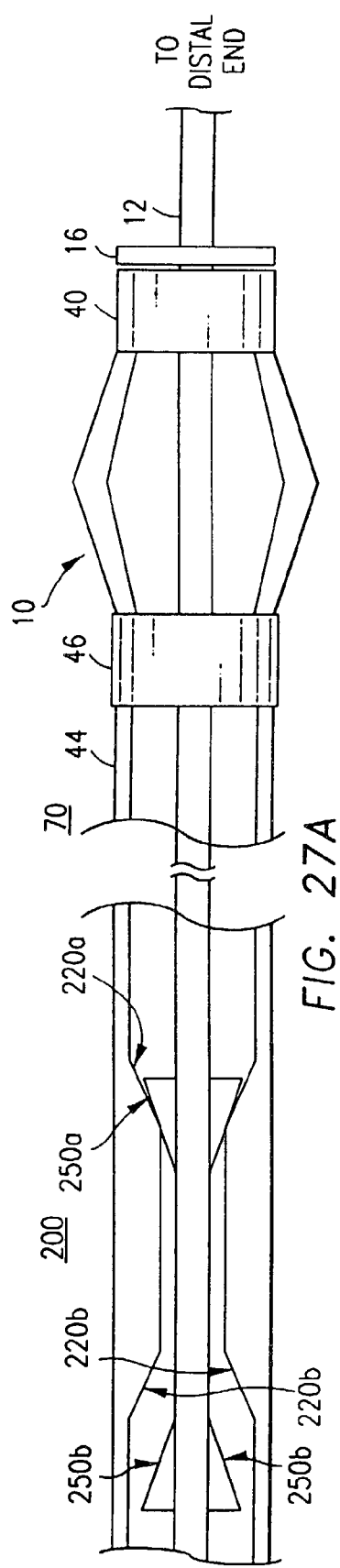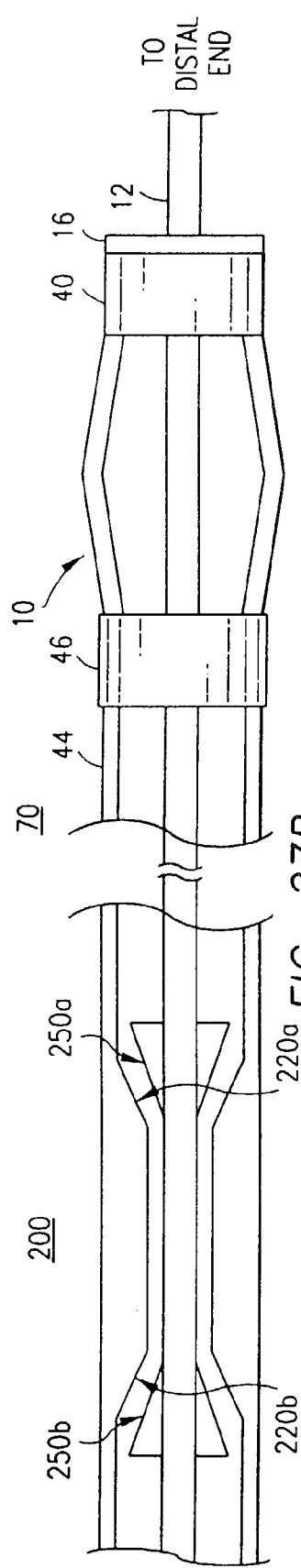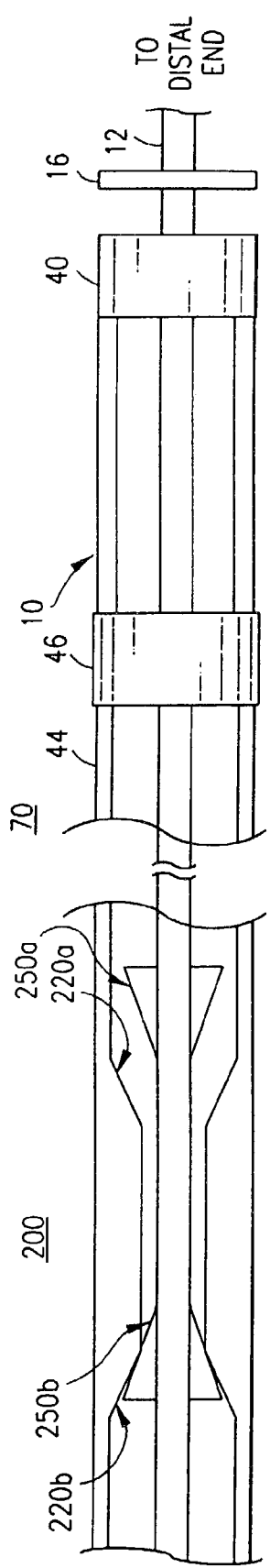

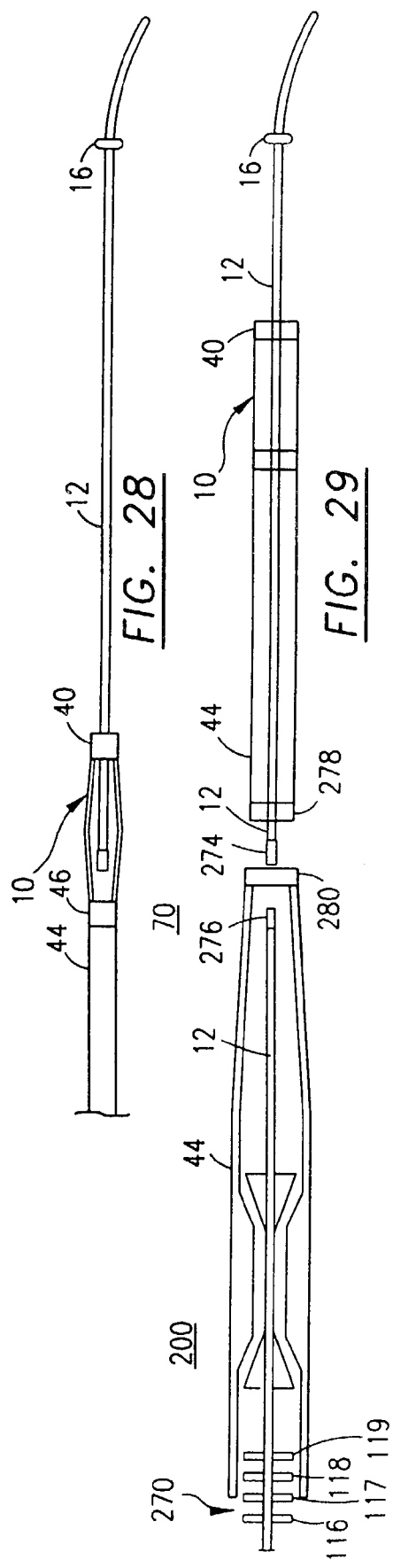
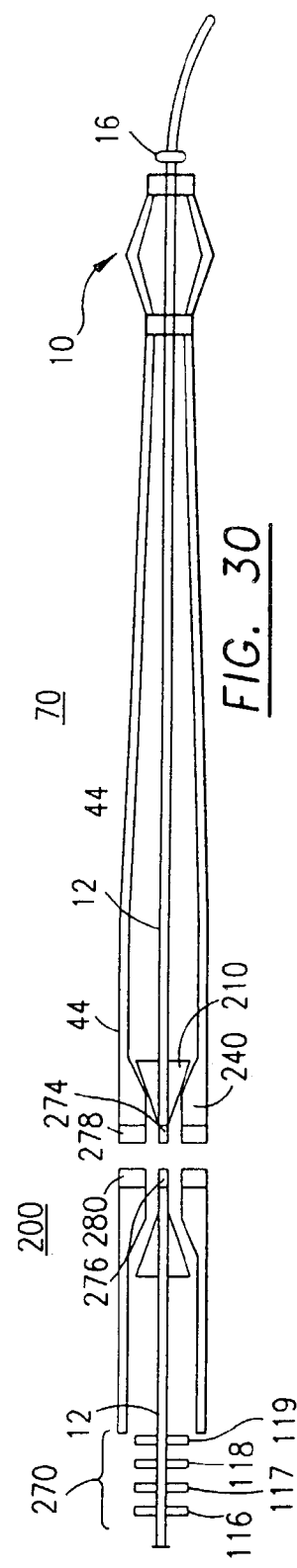
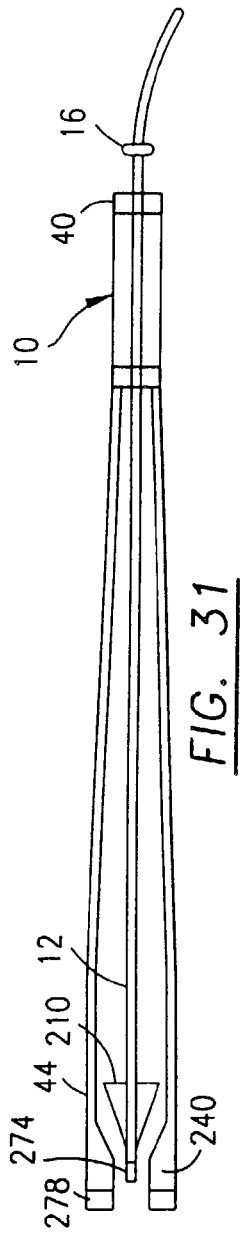
FIG. 28
FIG. 29
FIG. 30
FIG. 31

RADIOPAQUE LOCKING FRAME, FILTER AND FLEXIBLE END

This is a continuation-in-part of U.S. patent application Ser. No. 09/875,342 filed Jun. 6, 2001, now U.S. Pat. No. 6,537,296, which is a continuation-in-part of U.S. patent application Ser. No. 09/660,380 filed Sep. 12, 2000, now U.S. Pat. No. 6,344,049, which is a continuation of U.S. patent application Ser. No. 09/376,120 filed Aug. 17, 1999, which now U.S. Pat. No. 6,277,138, which claims benefit of provisional U.S. patent application Ser. No. 60/127,438 filed Apr. 1, 1999. The present application is also related to U.S. patent application Ser. No. 09/540,959 filed Mar. 31, 2000, and a continuation-in-part of U.S. patent application Ser. No. 09/376,120 filed Aug. 17, 1999, now U.S. Pat. No. 6,277,138.

The present invention relates to a system used to deploy a radiopaque radially expandable frame and an associated filter system which mounts onto the expandable frame. Additionally, the end piece of the system is flexible. The present invention also relates to a locking system utilized in connection with the deployment system to lock the radially expandable frame during its use. The filter system is used to capture embolic material during catheterization of a patient.

BACKGROUND OF THE INVENTION

During catheterization of a patient, a guide wire is directed through the patient's blood vessel to the site of interest. For example, the physician may wish to utilize a balloon catheter in order to enlarge a partially obstructed blood vessel at a certain location in the patient's vascular system. To do this, the physician utilizes a guide wire which is directed through the patient's vascular system to the particular site for balloon catheterization. Various medical devices are percutaneously inserted into the patient's blood vessel utilizing the guide wire. The balloon catheter, for example, is mounted at the distal end of an elongated tube. The guide wire is placed in the lumen of the balloon catheter tube such that the balloon catheter can be threaded over the guide wire, through the vascular system and placed at the site of interest by following the guide wire.

In order to enlarge a partially obstructed blood vessel, a physician may use various surgical techniques and biomedical devices or tools including balloon catheters, scrapers or other known medical devices. However, the utilization of these devices sometimes results in a release of an embolus (embolic material) which is an abnormal particle circulating in the blood. In order to reduce complications arising from these medical procedures, physicians sometime utilize filters disposed downstream of the site of interest. As used herein the term "downstream" refers to an item that is spaced a distance apart from a referenced item and in the direction of blood flow through the blood vessel.

U.S. Pat. No. 4,619,246 to Molgaard-Nielsen et al. discloses a collapsible filter basket. The basket includes a woven mesh but does not operate on a guide wire.

U.S. Pat. No. 4,723,549 to Wholey et al. discloses a filter which is expanded based upon inflation of a balloon acting as a donut mounted to expanding frame members of the filter disposed about the guide wire.

U.S. Pat. No. 5,053,008 to Bajaj discloses a filter which is expanded based upon inflation of a tubular balloon.

U.S. Pat. No. 5,108,419 to Reger et al. discloses a filter for capturing particles of plaque which includes a laterally (radially) collapsible bag with a plurality of longitudinally displaced filter cones therein. The bag has a draw string about its mouth which opens and closes the bag both laterally (to deploy or pull-up the conical filters) and longitudinally (to wrap the conical filters and the bag into a small-diameter shape). Each conical filter includes flexible tension supports which carry filter screens or mesh and which open and close based upon the respective longitudinal position of a generally static hub at the end of a guide wire running through the filter basket system. In another embodiment, a single conical filter is utilized with a filter stocking or collapsible bag thereabout. All the tension supports are flexible enough to wrap and twirl within the collapsible bag and wrap the conical filter(s) about the guide wire. Also, a draw string closes the collapsible bag in all embodiments. The flexible tension supports or radial ribs are resilient enough to provide force to spread the conical filter mesh across the lumen of the blood vessel.

U.S. Pat. No. 5,549,626 to Miller et al. discloses a filter deployed from the inside of a hollow tube by axial movement of an inner catheter.

U.S. Pat. No. 5,695,519 to Summers et al. discloses a wire, which controllably moves forward and aft, to open and close a generally conical filter by acting on the filter's mouth.

U.S. Pat. No. 5,810,874 to Lefebvre discloses a filter including strips that are radially opened by moving an inboard ring towards an outboard ring. The rings retain forward and aft ends of the strips. The filter can be detached from the guide wire.

U.S. Pat. No. 5,814,064 to Daniel et al. discloses one filter system which utilizes various types of inflatable ribs, tubes or struts and a second filter system wherein the filter material is deployed by longitudinal movement of a push-pull wire relative to a generally static distal end of a tube (see Daniel FIGS. 15–16B). In one embodiment, struts carry filter mesh and are forced radially outward by axial movement of a wire attached to the apex of the conical filter relative to a static tube end. In a collapsed position, the filter is disposed outboard of the static tube. In another embodiment, wire filter mesh has a conical memory shape such that when deployed outboard of a closed end cylinder, a conical filter is created by the memory shaped metallic filter. In another embodiment, only the open end of the conical filter has a memory shape. A further embodiment utilizes memory shaped filter mesh, a cinch wire and a push guide wire.

U.S. Pat. No. 5,911,734 to Tsugita et al. discloses a conical mesh filter with a proximal end strut structure connected to the distal end of a guide wire. Accordingly, the distal end of a guide wire is not downstream of the filter (see Tsugita FIGS. 2–8B). In another embodiment, the filter (conical or concave) is attached to radially outwardly biased struts. In a closed state, the biased struts are retained within a sheath. Upon axial movement of the guide wire relative to the sheath, the struts are moved beyond the sheath, they spring open to expand and deploy the filter. (See Tsugita FIGS. 10–11B). In a further embodiment, an egg beater filter is deployed. One embodiment of the egg beater filter utilizes a compressive spring which pulls fore and aft ends of expandable struts together, thereby radially expanding a filter basket with one side carrying filter mesh thereon. In other words, the filter is spring actuated. (Tsugita FIG. 15A). In another egg beater embodiment, pressure wires "spring" radially outward deploying conical cage wires which retain a mesh filter. (Tsugita FIG. 16). A scroll filter is also disclosed. A further embodiment discloses a filter with an expansion frame apparently made of memory shaped material. Tsugita FIG. 19 discloses a filter with a distally extending inner sheath having filter strut ends attached thereto and an outer sheath having the other filter strut ends attached thereto. To open the filter, the outer sheath is moved distally towards the inner sheath thereby causing the filter struts to buckle radially outward. The struts may be packed densely to form a filter or filter mesh material may be draped over the struts. In a different embodiment, an outer sleeve is longitudinally slitted. (Tsugita FIGS. 23, 23A). When the distal end of the slit outer sleeve is pulled proximally, the slitted region buckles radially outward to provide an egg beater filter. The expanded cage can be draped with filter mesh.

PCT Published Patent Application WO 96/01591 discloses a concave filter deployed by axially shortening the distance between the filter mouth and the filter apex (attached to a distal end of a guide wire). The filter mouth is sprung open by tethers fixed at one end to a static tube. A rod extends through the filter to its apex. The filter opens based upon the relative position of the filter apex on the rod (which extends beyond the apex to form the distal end of the guide wire) and the static tube.

OBJECTS OF THE INVENTION

It is an object of the present invention to provide a controllable deployment system for a radially expandable frame utilized during catheterization.

It is a further object of the present invention to provide an expandable frame with radiopaque frame struts having, in a preferred embodiment, a centrally located bent region.

It is an additional object of the present invention to provide a manually controlled and deployed expandable frame which can be used in conjunction with a filter for capturing embolic material flowing through a blood vessel.

It is a an additional object of the present invention to provide a controllable deployment system for a radially expandable frame utilized during catheterization that includes a friction locking mechanism at the proximal end of an actuator sleeve such that the deployment system can be locked during radial deployment and radial closure of the radially expandable frame.

SUMMARY OF THE INVENTION

The controllable deployment system for a radially expandable frame utilized during catheterization includes a guide wire with a stop at its distal end, a radiopaque radially expandable frame with distal and proximal frame ends wherein the guide wire freely passes through the proximal frame end, an elongated actuation sleeve having a flexible end piece through which freely passes the guide wire, and a friction locking mechanism located at the proximal end of the system which is defined by the proximal ends of the actuation sleeve and guide wire. The expandable frame includes radiopaque frame struts and has a closed, radially compact form and an open, radially expanded form. The frame, in the radially expanded form, has frame struts forming a pair of facing frustoconical frame structures. The guide wire extends through the expandable frame and the proximal end of the expandable frame is freely movable over the guide wire (likewise, the guide wire is freely movable within the frame end). The actuator, at its distal end, has a flexible end piece configured as a coil which enables the system to flex in excess of 90 degrees and to permit the frame and filter to be guided by the operator through the target vessel. The proximal end of the frame is coupled to an actuator sleeve. The actuator sleeve, at its proximal end, includes a friction locking mechanism having locking members with respective locking surfaces. The locking members are disposed on the proximal ends of the actuator sleeve and guide wire and include radially inboard and radially outboard locking surfaces, respectively. The locking mechanism permits the user to lock or hold static the actuator sleeve (and therefore, the expandable frame) with respect to the guide wire. The proximal ends of the guide wire and actuation sleeve may include detachable couplers allowing for removal of all or part of the locking mechanism from the deployment system. The system may also include tactile markers or indicia to indicate the frame's relative position to a fixed point on the guide wire.

BRIEF DESCRIPTION OF THE DRAWINGS

Further objects and advantages of the present invention are found in the detailed description of the preferred embodiments when taken in conjunction with the accompanying drawings in which:

FIG. 1 diagrammatically illustrates a cross-sectional view of the deployed filter device for capturing embolic material in a blood vessel;

FIG. 2 diagrammatically illustrates a collar at either the fore end or the aft end of the expandable frame and frame struts;

FIG. 3 diagrammatically illustrates the bent region of the frame strut and the partial wrap of non-perforated material around that bent region;

FIG. 4A diagrammatically illustrates the radially closed compact form of the expandable frame extending over the guide wire;

FIG. 4B diagrammatically illustrates the expandable frame filter in a radially closed compact form, on a guide wire and linked to an actuation tube and proximal lock with a catheter deployed at a proximal end of the filter, frame and actuator system;

FIG. 5 diagrammatically illustrates a cross-section of the radially closed compact form filter and illustrates the perforated filter material furled within the closed compact form of the expandable frame (the material being furled prior to deployment);

FIGS. 6A and 6B diagrammatically illustrate perspective views of the deployed expandable frame with the filter material on the outside of the frame struts and the filter material on the inside of the frame struts, respectively;

FIGS. 7 and 8A diagrammatically illustrate across-sectional view of the expandable frame and frame struts without the filter material and a perspective view of the deployed frame struts, respectively;

FIG. 8B diagrammatically illustrates a plane view of the transitional bent region of the frame struts;

FIG. 9 diagrammatically illustrates the expandable frame and deployed filter material mounted on the guide wire and utilized in connection with a balloon catheter;

FIGS. 10, 11 and 12 diagrammatically illustrate various stops and latch mechanisms operable in connection with the filter device;

FIG. 13 diagrammatically illustrates a further lock and latch system in order to operate the expandable frame;

FIG. 14 diagrammatically illustrates a threaded lock between the expandable frame filter and the actuation tube;

FIGS. 15A and 15B diagrammatically illustrate actuator tube latches at the proximal end of the guard wire, blood filter frame and actuator tube;

FIG. 16A diagrammatically illustrates a deployed filter and the position of the "light touch" latch at the proximal end of the actuator tube (and the introduction of a catheter tube over the filter system and actuator tube);

FIG. 16B diagrammatically illustrates a detailed view of a guide wire and the light touch, filter deployed latch system;

FIG. 16C diagrammatically illustrates the proximal end of the actuator tube latch;

FIG. 17 diagrammatically illustrates the catheter tube being introduced over the actuator tube;

FIGS. 18A, 18B and 18C diagrammatically illustrate the positional relationship of the catch or latch ring on the latch tube of the actuator for the fully radially closed position (FIG. 4A), a partially deployed position and a radially fully opened position (FIG. 1);

FIGS. 21A and 21B graphically and conceptually illustrate a friction locking mechanism utilized to lock the controllable deployment system in a forward or deployed position;

FIG. 22 diagrammatically illustrates a side view of the actuator sleeve and a locking mechanism to lock the controllable deployment system in a forward or deployed position;

FIGS. 23A, 23B diagrammatically illustrate a cross-sectional view of the locking mechanism illustrated in FIG. 22 from the perspective of line 23AB'–23AB";

FIG. 25A diagrammatically illustrates the controllable deployment system with a radially closed expandable frame and with a friction locking mechanism capable of locking the expandable frame in a radially deployed position;

FIG. 25B diagrammatically illustrates the controllable deployment system with a radially opened expandable frame and with a locking mechanism capable of locking the expandable frame in a radially closed position;

FIGS. 26A, 26B, 26C, 26D and 26E diagrammatically illustrate a friction locking mechanism capable of locking the deployment system during radial opening and closing of the expandable frame;

FIGS. 27A, 27B and 27C diagrammatically illustrate the deployment system with the locking mechanism and corresponding expandable frame in three different positions;

FIG. 28 diagrammatically illustrates the placement of the expandable frame and actuator sleeve over a two-piece segmented guide wire;

FIG. 29 diagrammatically illustrates the deployment system with a detachably coupled locking mechanism shown with the proximal end of the guide wire and actuation sleeve separated from the distal counterparts;

FIG. 30 diagrammatically illustrates the deployment system with a partially detachably coupled locking mechanism in a decoupled state; and FIG. 31 diagrammatically illustrates the deployment system with the actuator sleeve and expandable frame partially slid over the guide wire.

DETAILED DESCRIPTION OF THE PREFERRED EMBODIMENTS

Figure 4C:
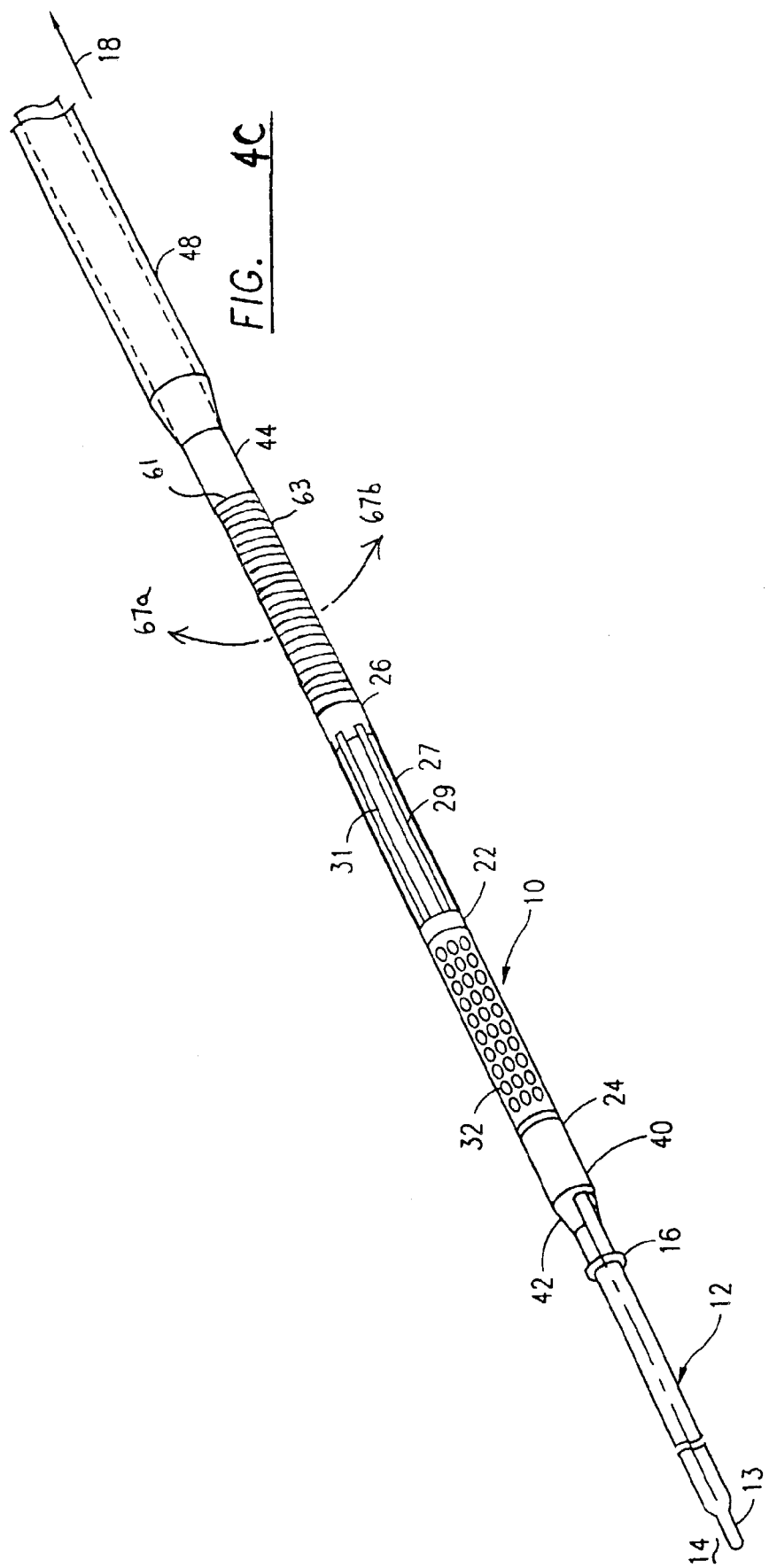
FIG. 4C diagrammatically illustrates frame filter, the actuator and the flexible end piece at the distal end of the actuator.

The present invention relates to a radiopaque radially expandable frame utilized during catheterization which includes a guide wire with a stop at its distal end, a radially expandable frame with distal and proximal frame ends wherein the guide wire freely passes through the proximal frame end, an elongated actuation sleeve with a highly flexible distal end piece through which freely passes the guide wire, and a friction locking mechanism located at the proximal end of the system which is defined by the proximal ends of the actuation sleeve and guide wire.

FIG. 1 diagrammatically illustrates a cross-sectional view of filter device 10 generally freely traveling on guide wire 12. In one embodiment, filter 10 can rotate and move longitudinally over guide wire 12 except for longitudinal movement beyond stop 16 towards distal end region 14 of the wire 12, otherwise the filter's proximal end freely moves longitudinally over the guide wire. More importantly, the guide wire 12 moves freely through filter device 10. Guide wire 12 has a proximal end shown by arrow 18. Stop 16 is mounted near the distal end of the guide wire.

Filter device 10 includes an expandable frame 20 formed of a plurality of radiopaque frame struts. The frame struts are coated with radiopaque material 41 such as gold or platinum such that the surgeon can see the filter on a radiologic monitor. Prior art devices only included radiopaque fore and aft rings. These radiopaque rings were sometimes difficult to see on radiologic monitors during the surgical operation. By coating the frame struts with gold (radiopaque material 41), the entire frame is visible on radiologic monitors. Further, the viewing angle for the radiologic sensing device is no longer an issue when the frame struts are coated. Frame struts 21, 23, 25 and 27 are identified in the cross-sectional view of FIG. 1. In a preferred embodiment, each of the frame struts 21, 23, 25 and 27 have a bent region 22. In a preferred embodiment, bent region 22 is preformed and is centrally located generally midway between the fore region 24 and the aft region 26 of expandable frame 20 on frame struts 21, 23, 25 and 27.

In the radially deployed state, expandable frame 20 forms a pair of facing, frustoconical frame structures 6, 28. The mouth of frustoconical frame structure 6 in the illustrated embodiment is upstream of fore end 24. As implied earlier, the term "upstream" refers to a position opposite the direction of blood flow 30 shown by the single headed arrow in FIG. 1.

Filter material 32 (typically PET material having perforations (generally 80 holes, 400 microns each)), is attached to frame struts 21, 23, 25 and 27 forming frustoconical frame structure 6. In FIG. 1, filter material 32 is attached to the outside of frame struts 21, 23, 25 and 27 (FIG. 1 representing a cross-sectional view of the deployed filter device 10). The aft end of filter material 32 (proximally disposed with respect to fore end 24 of filter device 10), has a non-perforated or drilled material region about bend transition region 22. This is better shown in FIG. 3 which is discussed below. The non-perforated region enhances a sealing against the lumen of the blood vessel.

One functional feature of the present invention involves the free movement of guide wire 12 within and through filter device 10. This freedom of movement, both radially and longitudinally along the length of the guide wire is accomplished by fore and aft collars 11, 34 of the filter 10. In another embodiment, the aft end of the frame struts is longitudinally freely disposed on the guide wire and the fore end of the frame struts is fixed to the guide wire.

FIG. 2 diagrammatically illustrates aft collar 34 movably disposed on guide wire 12. Similar numerals designate similar items throughout the drawings.

FIG. 3 diagrammatically illustrates frame strut 21 having bent transition region 22. Filter material 32 has a non-perforated material portion in bent region 22. Non-filtering region 22 generally restricts blood flow therethrough. This general flow resistant region 22 of material 32 operates differently compared to blood flow region of filter 32. Blood flow is generally shown by arrow 30 in FIG. 1. The material utilized for filter 32 in the blood flow region 33 (FIG. 3) is drilled or perforated. Other filters are known to persons of ordinary skill in the art. Generally, blood molecules flow through filter flow region of material 32 at region 33 but embolic material is captured by the filter thereat. These embolic materials are sometimes created by balloon catheterization, stenting or other surgical techniques acting on a surgical site upstream of filter device 10. This is illustrated and generally described later in connection with FIG. 9.

FIG. 4A diagrammatically illustrates filter device 10 in a radially compact form prior to deployment of the expandable frame. Guide wire 12 includes a coiled tapered end 13 at distal region 14. In some situations, the end 13 of guide wire 12 may be curved to enable the physician to better guide and place the guide wire in the desired vessel of the patient. See the curved blood vessel in FIG. 9. Filter device 10 includes a generally cylindrical fore end piece 40 and a tapered fore end segment 42. At aft end segment 26, filter device 10 includes an actuation sleeve or tube 44 which extends in direction 18 to the proximal end of the guide wire (not shown). FIG. 4A also shows a further surgical instrument 48 which is utilized by the physician to repair, replace, mount a stent or utilize another biomedical structure or tool at an upstream location with respect filter device 10. Instrument 48 is commonly called a catheter.

FIG. 4C diagrammatically illustrates filter device 10 with a flexible end piece 63 formed as part of actuator sleeve 44. Flexible end piece is a coil strain relief for the catheter assembly. The distal end 61 of actuator sleeve 44 tapers down to a coiled end piece section 63. The end piece section 63 is fixed to the proximal or aft collar 26 of the frame struts. Therefore, actuator sleeve 44 includes a coiled tapered end 63 at its distal region which permits the entire distal end assembly, filter 10, tip 12 and frame struts 29 et seq., to flex in directions 67a and 67b as needed by the surgeon. This high degree of flexibility, typically in excess of 90 degrees from the axial centerline of the guide wire, is helpful to guide the system through the vascular system of the patient. Additionally, the flexible end piece 63 provides a smooth transition to the filter basket. See the curved blood vessel in FIG. 9. FIG. 4C also shows a further surgical instrument 48 which is utilized by the physician to repair, replace, mount a stent or utilize another biomedical structure or tool at an upstream location with respect filter device 10.

In general, the operation of filter device 10 is as follows. The physician deploys the guide wire 12 in the blood vessel of the patient at or near the surgical site of interest. Filter device 10 is customarily carried by guide wire 12 through the vascular system. Hence in one embodiment, rotational and longitudinal freedom of movement of filter device 10 (integrated with actuation sleeve 44) with respect to guide wire 12 is important. In another, only the rear end of the frame of struts moves longitudinally with respect to the guide wire. The filter device 10 and actuation sleeve 44 runs with guide wire 12 as an integrated system or unit. See FIG. 4B.

Either before or after the physician threads or places balloon catheter or other surgical device 48 over the actuation sleeve 44 and hence over guide wire 12, the physician may radially deploy the expandable frame 10 in the following manner. The fore end 42 of expandable filter device 10 contacts stop 16 on guide wire 12. Otherwise, the for end is fixed to the guide wire. This position is shown diagrammatically in FIG. 1. Before such contact, the physician may twist (torque) the guide wire through the vascular system. The surgeon sees the filter via radiologic monitoring system and the radiopaque or gold coating on the frame struts greatly assists this viewing process. The guide wire freely moves rotatably and longitudinally through the filter device 10 (except for movement beyond stop 16).

At that point in time or shortly thereafter at stop 16 (or otherwise if the filter is fixed to the guide wire end), the physician continues to exert a forward force on filter actuation tube or sleeve 44 in the longitudinal or axial direction with respect to guide wire 12 (e.g. pulling the guide wire while pushing actuation tube 44) thereby causing compression of filter 10 and sleeve 44 and frame struts 21, 23, 25, 27, 28, 29 and 31 and causing the struts to radially expand to the position shown in FIG. 1. Radial expansion is limited by either the interior size of the blood vessel or the mechanical limits of the non-filter material about bent region 22. In the pre-deployed state and in a preferred embodiment, filter material 32 is furled within radial compact structure.

Figure 19:
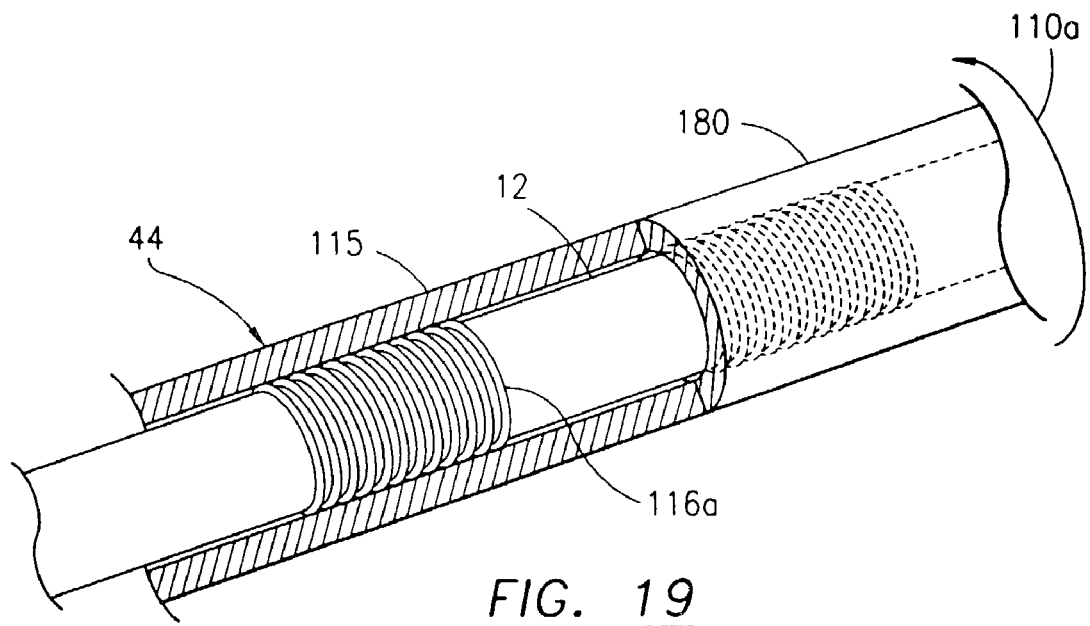
FIG. 19 diagrammatically illustrates a thread control to manually deploy the filter, the thread control established between the threaded catch on the guide wire and the threads at the proximal end of the actuator cylinder.

The operation of actuation sleeve 44 and actuator piece 115 (shown in FIG. 4B) is discussed later in detail in connection with FIGS. 15A, 15B, 16A, 17, 16B, 16C, 18A, 18B, 18C. Alternative actuator and latch systems are shown in FIG. 19.

FIG. 5 diagrammatically shows filter material 32 furled or disposed in the interior of the closed radially compact form of expandable frame 20. FIG. 5 shows expandable frame 20 with frame struts 21, 23, 25, 27, 29 and 31.

After deployment and formation of frustoconical frame structures 6, 28, the physician (a) threads device 48 (e.g. catheter 48) over guide wire 12 and actuation sleeve 44 and (b) activates the balloon catheter or other biomedical device 48 which is upstream, relative to blood flow, of the deployed expandable frame 10. After the surgical procedure with biomedical device 48, expandable frame 10 is collapsed by the physician or other medical technician by longitudinally pulling actuation sleeve 44 in a proximal direction relative to the guide wire 12. The collapse of expandable frame 10 is achieved by (a) temporary retention of the fore end 40, 42 of expandable frame 10 or (b) closing spring action of the frame or (c) both retention and closing spring action. Temporary retention of the frame is shown diagrammatically with certain lock or latch structures in FIGS. 10–12 which are discussed later. Upon collapse, filter 32 captures and entraps embolic material and this embolic material is withdrawn from the blood vessel of the patient by proximal withdrawal of actuation sleeve 44 and expandable frame filter device 10 over guide wire 12.

FIGS. 6A and 6B diagrammatically illustrate filter material 32 on the outside of frame struts 21, 23, 25, 27, 29 and 31 and on the inside of those frame struts, respectively.

Figure 6C:
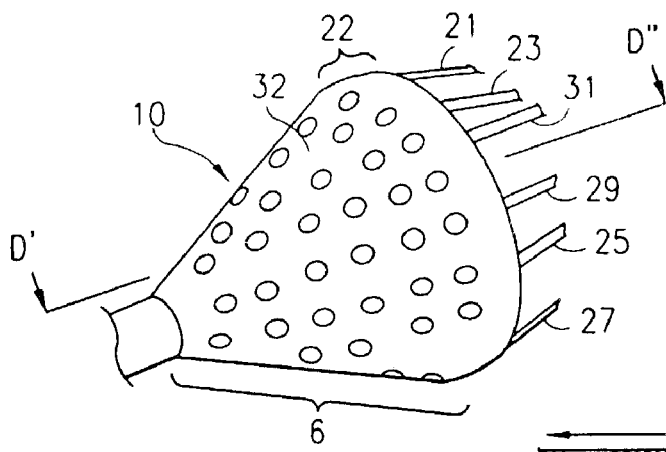
FIG. 6C diagrammatically illustrates a perspective view of a deployed expandable frame with perforated filter material without the delineation of the bent region for the frame members.

FIG. 6C diagrammatically illustrates filter device 10 in a radially deployed state. Filter material 32 has a filtering region substantially covering frustoconical frame structure 6. However, there is no clear demarcation (other than the absence of holes and passage ways) between filter material 32 and peripheral bend region 22 which is a non-filter region.

Figure 6D:
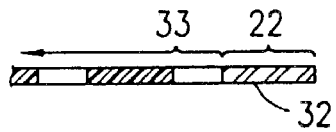
FIG. 6D diagrammatically illustrates the non-perforated material disposed around the bent transition region of the frame and the beginning of the perforated filter area.

FIG. 6D diagrammatically illustrates a plane view showing non-filter region 22 and the filter region 33 from the perspective of a portion of section line D'–D" in FIG. 6C.

Figure 6E:
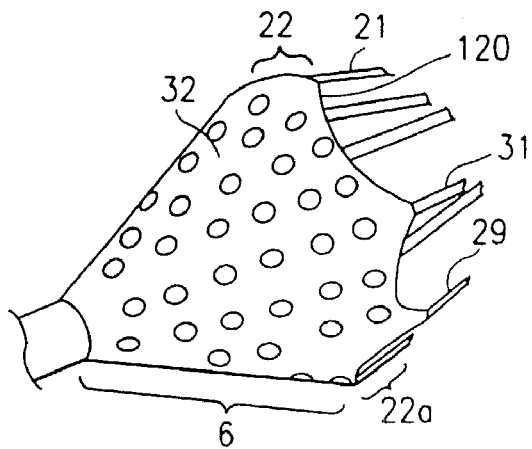
FIGS. 6E, 6F and 6G diagrammatically illustrate a deployed expandable frame in a fully open state with filter material having a scalloped edge, a partially closed state, and a further closed state (the fully closed state diagrammatically illustrated in FIGS. 4A and 5)
Figure 6F:
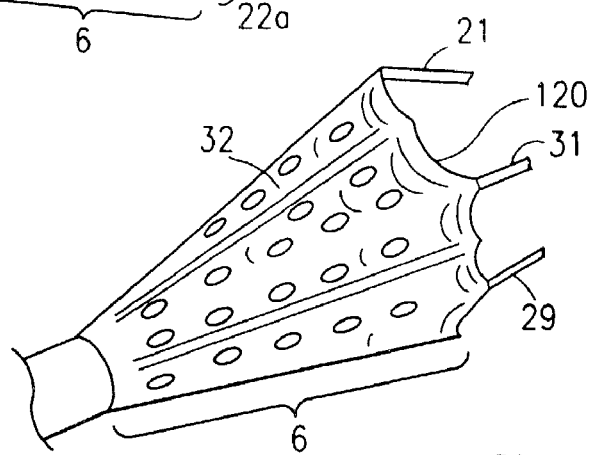
Figure 6G:
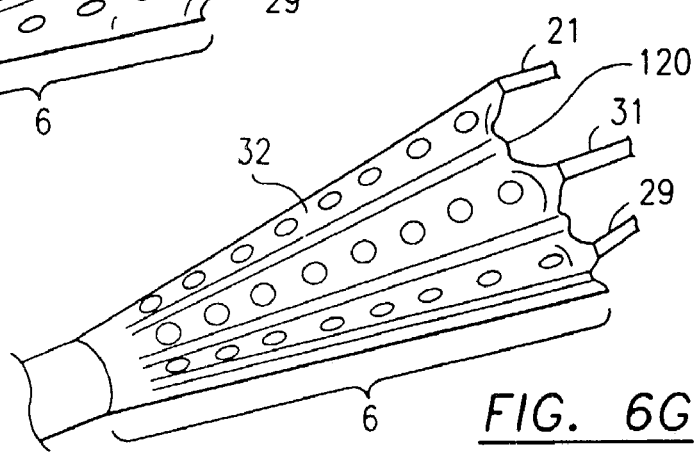

FIGS. 6E, 6F and 6G diagrammatically show a scalloped edge in the non-filter bend region 22–22a. FIGS. 6F and 6G diagrammatically illustrate various collapsed states or positions for frustoconical frame structure 6. The utilization of scallop or concave edge regions spanning adjacent struts (see concave or scallop edge region 120 between the adjacent struts 21, 31), enable the filter material 32 to furl and gather either beneath the frame strut (FIG. 6B) or about the frame strut (FIG. 6A) in order to achieve radial containment upon collapse and prior to withdrawal similar to that illustrated in FIG. 5. FIG. 6F diagrammatically illustrates that filter material 32 gathers and furls upon partial radial collapse of frustoconical frame structure 6 due to the concave or scallop nature of the material between the complementary frame struts, that is complementary to adjacent struts 21, 31. FIG. 6G shows that concave edge 120 promotes gathering of filter material 32 between the complementary frame struts associated with struts 21, 31. As used herein, the term "complementary frame struts" refers to struts attached to adjacent struts 21, 31 and struts which form the frustoconical frame structure 6 upon which is disposed filter material 32.

FIGS. 6E, 6F and 6G diagrammatically illustrates that filter device 10 can be constructed to collapse and gather the filter material 32 as an umbrella.

FIGS. 7 and 8A diagrammatically illustrate a cross sectional view and a perspective view of the deployed frame struts 21, 23, 25, 27, 29 and 31. FIG. 8A diagrammatically shows an additional frame strut 33. Accordingly, filter device 10 can include a plurality of frame struts if necessary. FIG. 8A also diagrammatically shows the bend transition region 33a for frame strut 33. In a preferred embodiment the frame struts are preformed (pre-shaped) and bent at transition region 33a such that upon axial or longitudinal compression between stop 16 and the proximal region of guide 12, the frame struts expand at a predetermined common point. Preferably, the common point is centrally located on the struts. Preferably, the struts also have a "memory" which biases the struts to a closed position. See FIG. 4A. FIG. 8B shows a further enhancement wherein the struts are notched at 35a, 35b to facilitate a consistent and predictable bent region 33a. Notches or cutouts 35a, 35b are preferably disposed at the midpoint of complementary frame strut members.

FIG. 9 diagrammatically illustrates the deployed filter device 10 disposed in a blood vessel 90 of a patient. Guide wire 12 has been generally placed near the site of interest and slightly distally beyond the site of interest. The site of interest is partial blockage or occlusion 92 in blood vessel 90 of the patient. It is desirable to have guide wire 12 move, with respect to filter 10, freely both radially and longitudinally except filter 10 will not move distally beyond stop 16 on guide wire 12. This freedom of movement (two degrees of freedom) permits the guide wire to move through the blood vessel 90 and particularly about blood vessel bend 91. In operation, the physician deploys expandable frame 10 downstream of medical device or catheter 48 relative to blood flow 30. Device 48 is placed and runs over the outside of actuation tube or sleeve 44 which is operatively associated with aft end region 26 of filter device 10. By longitudinal compression (a force directed distally by the physician via actuation sleeve 44), filter device 10 radially expands thereby deploying filter material 32. Filter material 32 has a filter size (perforations or hole diameter 400 microns) adequate to capture embolic material which may be dislodged by the medical procedure at site 92 upstream of filter 10. Biomedical device 48 in FIG. 9 is a general illustration of a balloon catheter. Actuator sleeve 44 and the collapsed filter device 10 easily passes within a 0.05 inch lumen of catheter 48.

FIGS. 10–12 diagrammatically illustrate various stop configurations and latches to enable (a) deployment of filter material 32 and (b) collapse and retrieval of the filter device 10 from surgical site 92. FIG. 10 illustrates stop 16 as a ring attached to guide wire 12. The fore end piece 42 of filter device 10 includes a channel 50 which is complementary or slightly smaller than guide ring-stop 16. When guide ring 16 is placed in channel 50 of fore piece 42, filter device 10 is latched onto and temporarily locked to guide wire 12. This latch or lock permits both radial deployment of filter 32 (see FIGS. 1 and 9) and also permits the closure of the filter by proximally moving actuation sleeve 44 in a direction away from ring stop 16. This movement is relative to the guide wire.

FIG. 11 shows a cylindrical stop 16 having a generally cylindrical body 17 and a protruding ring 19. Fore end piece 42 of filter device 10 includes a complementary cavity 50, complementary to the shape of ring like protrusion 19 and a larger fore end cavity 51 which is complementary to the aft end shape of cylindrical fixed stop collar 17. The operation is substantially similar as that discussed above in connection with FIG. 10.

FIG. 12 diagrammatically illustrates another configuration of stop and latch 16 which includes a radially inboard aft channel 13. The fore end 42 of filter device 10 includes a protruding end piece 52 that is complementary to aft end channel 13 of fixed lock collar stop 16. Again, the physician distally moves filter device 10 until fore end key piece 52 locks into channel 13 of collar stop 16. Further distal movement of actuation sleeve 44 over guide wire 12 (which is static or "not moving") causes radial deployment of the expandable frame struts of filter device 10. To withdraw the filter device 10, the physician proximally pulls actuation sleeve 44 thereby collapsing the frame struts, collapsing the frustoconical frame structure 6 (FIG. 1), collapsing filter material 32 and capturing any embolic material which did not pass through filter material 32. Typically, the collapse is assisted by the closing spring action of the frame struts. The lock and latch system consisting of channel 13 and key latch 52 is strong enough to result in the collapse of the frame strut and the filter mesh. Upon further proximal movement of actuation sleeve 44 and after full collapse of the expandable frame 10, the locking force of channel 13 and lock latch 52 is overcome by the pulling force of the physician, fore end latch piece 52 exits locking channel 13 and the filter device 10 is withdrawn from the blood vessel 90.

FIG. 13 diagrammatically illustrates an aft end locking latch system. Aft end region 26 of filter device 10 includes an aft cylindrical end 55 with a ring collar 56. Actuation sleeve 44 includes a fore end piece 45 with a locking complementary channel 47 and a longitudinally larger mating channel 49. Mating channel 49 passes over the aft end of aft member 55 of filter device 10. Locking channel 47 is complementary to the shape of collar protrusion 56 thereby enabling the actuation sleeve 44 to latch onto the ring collar 56. In this manner, the actuation sleeve 44 can be attached and detached from the filter device 10. If detached, the balloon catheter or other biomedical device 48 travels directly over the guide wire rather than over actuation sleeve 44. The forces necessary to latch and unlatch the fore end 40, 42 of filter device 10 must be commensurate or balanced with respect to the locking and latching features on the aft end 55, 56 of filter device 10.

In addition, FIG. 14 shows that aft end piece 55 of filter 10 can be threaded and carry a set of threads 60 which are complementary to thread set 62 on actuation sleeve 44. By locking and latching the fore end of filter 10 via one or more of the systems shown in FIGS. 10–12, the actuation sleeve 44 can be threaded onto aft piece 55 of filter device 10. Of course, the male and female thread features of the system shown in FIG. 14 can be reversed such that aft 55 defines female threads and actuation sleeve 44 carries male threads.

As discussed earlier in connection with FIG. 4B, filter 10 operates based upon longitudinal movement of actuator sleeve or tube 44. Longitudinal movement 112 is noted with respect to filter device 10, actuator 44 with respect to guide wire 12.

It is important that the physician be notified tactually (via touch) and visually that filter device 10 is approaching distal end stop 16 which is permanently affixed to guide wire 12. In order to provide such notification, FIG. 4B utilizes three temporary stops or latch points 116, 117, 118. However, it should be noted that only a single temporary stop or latch point 116 may be utilized in connection with the present invention.

FIG. 15A diagrammatically illustrates a partial, cross-sectional detailed view of actuator piece 115 which is part of actuator sleeve 44. Preferably, actuator piece 115 is cylindrical and is made with a more rigid material as compared with actuator sleeve 44. Most of the materials utilized in connection with filter device 10 and actuator sleeve 44 are stainless steel. Filter struts are preferably Ni Ti. Filter material 32 is preferably drilled (with a laser) and filter material 32 and non-filter region 22 is preferably made of PET. Actuator piece 115 is preferably a tube of Ni Ti. Other materials may be utilized as known to persons of ordinary skill in the art.

In the illustrated embodiment of FIGS. 4B and 15A, three stops (temporary stops) or latch points 116, 117 and 118 are utilized. Temporary stop 118 provides an initial indication to the physician that filter device 10 is soon approaching distal end stop 16. Intermediate temporary stop 117 is a tactile and a visual notice of the close approach of nose piece 42 to stop 16.

FIG. 15A diagrammatically shows that temporary stop 117 has a slightly larger outside diameter as compared with the inside diameter of actuator piece 115. As described later, actuator piece 115 has a longitudinal slot 132 therethrough which permits the aft region of actuator piece 115 to move radially. Accordingly, the physician is permitted to hold or withdraw actuator piece 115 in the direction shown by arrow 112a in FIG. 15A thereby causing actuator piece 115 to radially expand and "jump over" temporary stop 117.

FIG. 15B diagrammatically shows the slight radial overlap between temporary stop 116 and actuator piece 115. All latch points 116, 117, 118 have a similar radial relationship with respect to the interior or inner diameter of actuator piece 115. Accordingly, every time aft edge 134 of actuator piece 115 passes over temporary stop or latch points 116, 117, 118, the physician is tactually notified and can visually confirm the position of filter device 10 in relation to distal end stop 16. By providing consistent, repeatable and reportable distance relationships between stops 116, 117, 118 and the radial deployment and/or longitudinal position of the filter basket and distal end stop 16, the physician or the operator can easily control the distance and radial expansion (and contraction) of filter device 10 in relation to end stop 16.

More importantly, distal end stop 116 is utilized to expand filter device 10 as shown in FIG. 16A.

FIG. 16A diagrammatically illustrates a radially expanded filter device 10 which is achieved by the physician longitudinally pushing actuator sleeve 44 such that actuator piece 115 is distally located or longitudinally inboard with respect to temporary stop or latch point 116. Even with filter 10 radially deployed as shown in FIG. 16A, the physician can easily rotate guide wire 12 as shown by double headed arrow 110 and also move the entire guide wire and temporarily latched and deployed filter 10 in the direction shown by double headed arrow 112. FIG. 16A also shows that biomedical device or catheter 48 can be fed over temporary stops 116, 117, 118, actuator piece 115, actuator sleeve 44 and lead to a point near the aft end of deployed filter device 10.

FIG. 17 shows catheter 48 extending over actuator sleeve 44. Guide wire 12 protrudes proximally out of the rear end of catheter biomedical instrument 48.

In order to radially collapse filter device 10, the physician pulls actuator piece 115 in the direction shown by arrow 112a in FIG. 16A thereby overcoming the temporary latch 116, partially radially expanding actuator piece 115 and longitudinally withdrawing actuator sleeve 44 with respect to guide wire 12. As discussed earlier, the frame struts form filter device 10 preferably have a memory which biases the frame struts to a closed position. This feature enhances closure of the filter device 10.

FIG. 16B diagrammatically illustrates actuator piece 115 disposed at the proximal end of actuator sleeve 44. Actuator piece 115 includes a longitudinal slot 132. The proximal end 134 of actuator piece 115 is temporarily caught on latch point 116. It should be noted that actuator piece 115 may have a plurality of slots or may be made of a material which easily radially expands in order to overcome temporary latch points 116, 117, 118. Also, rather than having square peripheral edges, the latch point edges may be rounded. Other latch point shapes may be utilized.

FIG. 16C provides a detailed view of slot 132 and actuator piece 15.

FIGS. 18A, 18B and 18C diagrammatically illustrate the various positional aspects of actuator piece 115 in relation to critical temporary latch point 116. In FIG. 18A, latch point 116 is at an inboard position relative to actuator piece 115. Temporary latch point 116 is "critical" to the physician's ability to (a) locate the expandable frame's position relative to a fixed point on the guide wire and/or (b) determine the radial span of the frame. The physician can easily rotate guide wire 12 in the direction shown by double headed arrow 110 and may also longitudinally move guide wire 12 in relation to filter device 10 as shown by double headed arrow 112. In FIG. 18B, latch point 116 is disposed beneath slot 132. This position provides several advantages. First, the physician may tactually and visually see temporary latch 116 as it travels within slot 132. Preferably, upon visual or tactile confirmation that sleeve 115 as been placed such that latch 116 is adjacent slot 132, the filter device 10 is radially deployed at various positionally related states of radial deployment. In other words, when actuator piece 115 is positioned such that temporary latch 116 is disposed at or near the inboard or distal end of slot 132, the frustoconical frame 6 begins to radially open filter material 32 (assuming that the actuator is moving distally with respect to a stationary guide wire). At the slot mid-point (FIG. 18B), frustoconical frame 6 is approximately 50% radially open. When actuator piece 115 is completely disposed inboard or at a distal position relative to temporary latch point 116 (FIG. 18C), frustoconical frame structure 6 is fully radially deployed.

Figure 20:
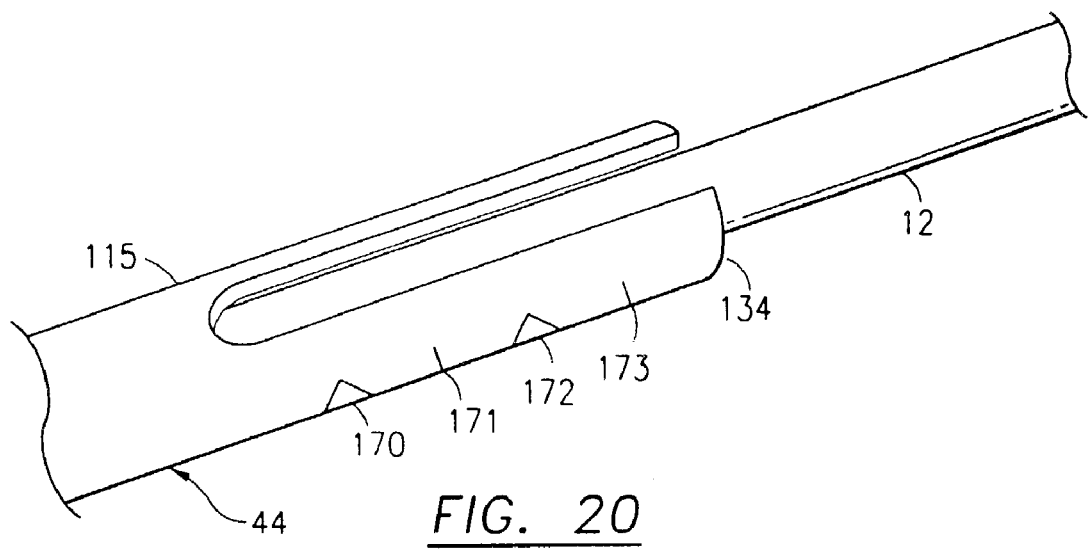
FIG. 20 diagrammatically illustrates a latch cylinder with indicia marking the radial deployment of the filter at the distal end of the system.

FIG. 20 diagrammatical illustrates actuator piece 115 having various indicia or markings 170, 171, 172, 173 which show and provide a visual indication to the physician that the filter device 10 begins its opening sequence (indicia 170), is 25% open (indicia 171), is 50% open (indicia 172), is 75% open (point 173) and is fully open when proximal end 134 of actuator piece 115 is located at an inboard or distal position relative to temporary latch point 116. Indicia 170, 171, 172 and 173 are used in connection with temporary latch points on the guide wire as explained above in connection with FIGS. 18A–18C to show radial span and/or relative longitudinal position of the frame on the guide wire.

Other types of temporary latches or stops can be provided at the proximal end of actuator sleeve 44. For example, FIG. 19 diagrammatically illustrates that critical latch 116a has a male thread defined thereon and a proximal region 180 of actuator piece 115 has a female thread thereon. When the male thread of latch 116a mates with the female thread on proximal region 180 of actuator piece 115, filter device 10 begins to radially deploy. Upon rotation in a direction, for example direction 110a, the physician by rotating actuator piece 115 radially expands filter device 10 by further threading threaded member section 180 of actuator piece 115 over threaded latch 116a. Threaded temporary latch 116a may be used with the slot 132 (FIG. 16B) or indicia 170 et seq. (FIG. 20) to provide visual positional data regarding the system.

In some situations, embolic material trapped in the filter may limit full radial closure of the filter (to a state similar to FIG. 4A). If the embolic material carrying filter is radially large (relative to the fully closed position FIG. 4A), the physician, subsequent to the withdrawal of the catheter, (a) places a guide wire extender on the proximal end of the guide wire; (b) longitudinally withdraws the actuator tube and the "full" filter basket while leaving the distal end of the guide wire at the point of interest; (c) withdraws the filter basket proximally beyond the guide wire extender; (d) unmounts the extender from the guide wire proper; and (e) proceeds with other surgical techniques (which may include the use of a new filter basket and/or a catheter or stent). This procedure is particularly useful when a stent is placed in the patient's blood vessel.

Some surgical techniques utilizing the deployment system 70 described herein may be made easier and less risky if the expandable frame 20 can be locked in a radially open (deployed) state or in a radially closed state. For example, if a medical practitioner was performing a balloon angioplasty, it would helpful to have a filter locked in a deployed state downstream from the target site of the atherosclerotically obstructed artery in order to capture any embolic materials loosened during the procedure. As discussed above in connection with the filter basket, some circumstances require that the expandable basket be locked in substantially radially open and radially closed states. FIGS. 21 through 31 illustrate a locking mechanism used to lock the distally located radially expandable frame 20 (with or without the filter) in a closed, radially compact form, and in an open, radially expanded form.

FIGS. 21A and 21B graphically and conceptually illustrate a locking mechanism 200 preferably located at the proximal end of deployment system 70. The friction lock could be deployed at a distal position if a lock or latch mechanism is necessary thereat. Locking mechanism 200 includes a first locking member 210 with a radially inboard sloped locking surface 220. First locking member 210 is preferably disposed on the proximal end of the actuator sleeve 44 (see FIG. 22) or actuator piece 115 (see FIGS. 18A, 18B and 18C). First locking member 210 may be made of a plastic or metallic material, and may be added to actuator sleeve 44 (see FIG. 22), or may be cast as part of a mold, rolled or formed including actuator sleeve 44 (see FIG. 24). Locking mechanism 200 also includes a second locking member 240 with a radially outboard sloped locking surface 250. Second locking member 240 is disposed on the proximal end of guide wire 12 near or adjacent locking member 210. Likewise, second locking member 240 may be made of a plastic or metallic material, and may be added to guide wire 12 (FIG. 21A), or may be cast, rolled or formed as part of the proximal end of guide wire 12 (FIG. 21B).

In FIGS. 21A and 21B, radially inboard locking surface 220 includes a proximal end 224 being radially further inboard than distal end 226, thus defining a sloping or sloped surface. Radially outboard locking surface 250 has a proximal end 254 which is radially closer or has a radial dimension generally similar to guide wire 12 than the radial span or radial dimension of distal end 256 which is larger than the span at end 254. In FIG. 21A, radially inboard locking surface 220 defines a radially inboard friction face with a substantially continuous, substantially constant slope. In other embodiments, the slope may change over the axial span of the lock (from end 254 to end 256). Similarly, radially outboard locking surface 250 defines a radially outboard friction face with a generally continuous, substantially constant slope. In FIG. 21B, radially inboard locking surface 220 defines a radially inboard face with a substantially constant slope, and includes numerous cavities or indentations 228. Alternatively, a single protrusion or groove may be utilized to provide a single, simple latch on the friction face. Radially outboard locking surface 250 defines a radially outboard face with a substantially constant slope, and includes numerous projections or protrusions 258. The cavities may be formed on surface 250 and the protrusions on surface 220.

FIG. 22 diagrammatically illustrates locking mechanism 200 on the filter or expandable frame deployment system of the present invention. Locking mechanism 200 in FIG. 22 is substantially similar to locking mechanism 200 in FIG. 21A. FIG. 22 includes actuator sleeve 44 attached to locking members 210.

FIG. 23A diagrammatically illustrates a cross-sectional view of locking mechanism 200 in FIG. 22 from the perspective of 23AB'–23AB". In FIG. 23A, first locking member 210 consists of two parts 210a, 210b, each attached, formed or mounted on actuator sleeve 44. Each part has a corresponding radially inboard locking surface 220a, 220b. Second locking member 240 which is attached, formed or mounted on guide wire 12 has a radially outboard locking surface 250. The sloped bar-shaped locking members 210a, 210b and surfaces may be formed on the guide wire 12 and the circumferentially uniform locking members may be formed on the actuator sleeve 44.

FIG. 23B also diagrammatically illustrates a cross-sectional view of an alternative embodiment of locking mechanism 200 in FIG. 22 from the perspective of 23AB'–23AB". In FIG. 23B, first locking member 210 is has a circumferentially uniform surface disposed on actuator sleeve 44 with radially inboard locking surface 220. Second locking member 240, which is attached to guide wire 12, has a circumferentially uniform surface with locking radially outboard surface 250. Other alternatives include a uniform first locking member 210 with a multiple, radially extending arm second locking member 240, and a multiple radially extending arm first locking member 210 with a uniform second locking member 240.

Figure 24:
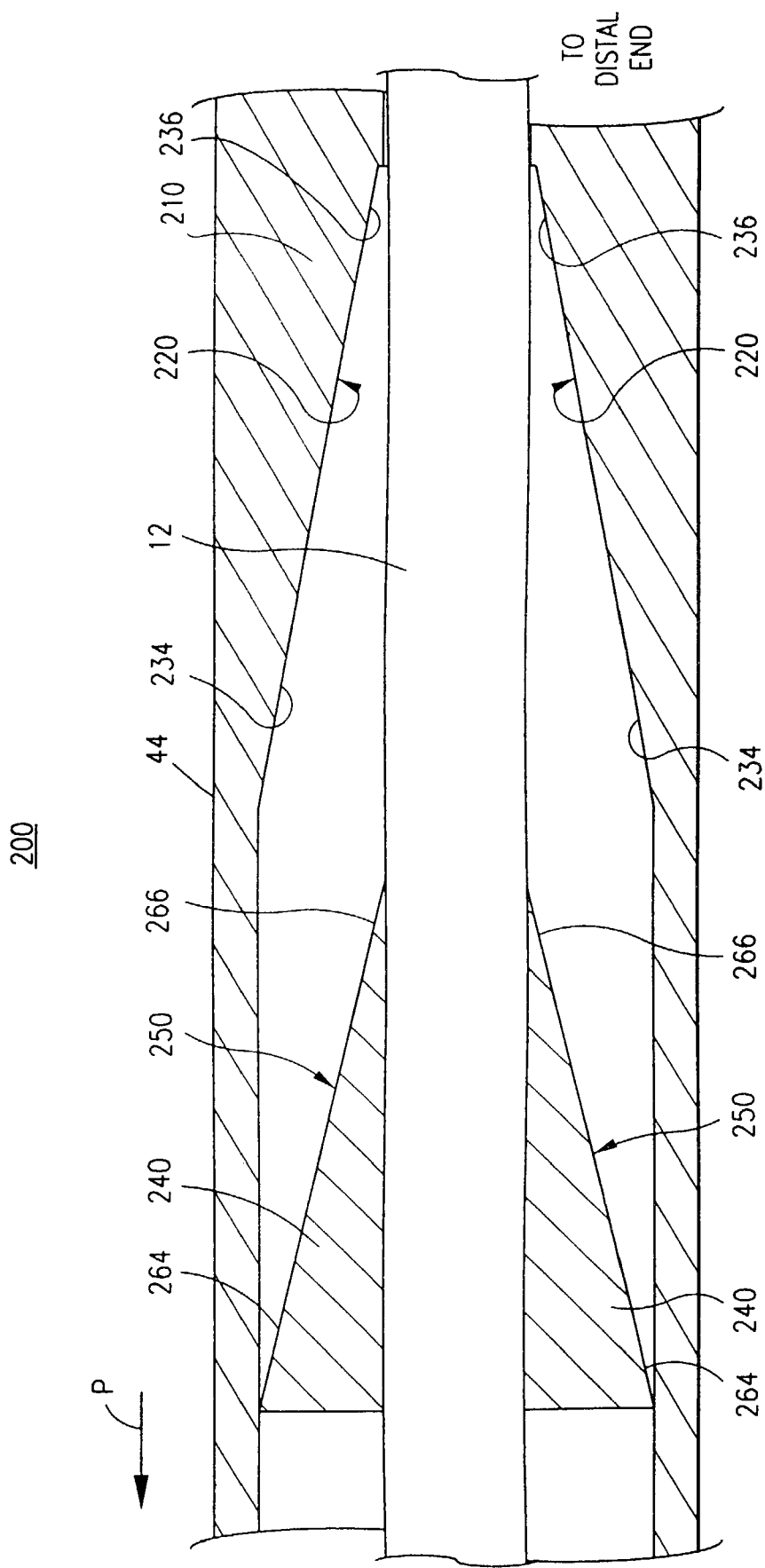
FIG. 24 diagrammatically illustrates the actuator sleeve and a locking mechanism to lock the controllable deployment system in a rearward or non-deployed position.

FIG. 24 diagrammatically illustrates another embodiment of locking mechanism 200 located at the proximal end of filter or frame deployment system 70. In FIG. 24, radially inboard locking surface 220 is shown with distal end 236 being radially further inboard than proximal end 234. Radially outboard locking surface 250 is shown with proximal end 264 being radially further outboard than distal end 266. Radially inboard locking surface 220 defines a radially inboard friction face with a generally continuous, substantially constant slope. Similarly, radially outboard locking surface 250 defines a radially outboard friction face with a generally continuous, substantially constant slope.

FIG. 25A diagrammatically illustrates filter or frame deployment system 70, including locking mechanism 200, actuator sleeve 44 and expandable frame 10. Expandable frame 10 is in a radially closed form. Expandable frame 10 includes several frame struts (see FIGS. 1, 6A and 8A for example) which are diagrammatically illustrated by struts 21 and 25, each attached to aft frame collar 46 and fore frame collar 40. Guide wire 12 operates through locking member 200, and passes through actuator sleeve 44 and expandable frame 10 and is freely movable both radially and longitudinally except that actuator sleeve 44 and expandable frame 10 cannot move longitudinally beyond distal stop 16 (located at the distal end of guide wire 12). In FIG. 25A, expandable frame 10 is distally located on guide wire 12 such that frame collar 40 is adjacent stop 16. Radially outboard locking member 240 on guide wire 12 defines a bullet-shape or missile-shape. Radially outboard locking surface 250 defines a smooth, continuous convex shape. Radially inboard locking member 210 on actuator sleeve 44 includes radially inboard locking surface 220 which defines a corresponding smooth, continuous, concave bowl-like shape.

FIG. 25B diagrammatically illustrates deployment system 70, including locking mechanism 200, actuator sleeve 44 and expandable frame 10. In FIG. 25B, expandable frame 10 is in a partially radially open form. Accordingly, aft frame collar 46 and fore frame collar 40 are longitudinally closer together, giving expandable frame 10 a longitudinally foreshortened form. In FIG. 25B, expandable frame 10 is distally located on guide wire 12 such that frame collar 40 is adjacent stop 16. Radially outboard locking member 240 defines a frustoconical shape. Radially outboard locking surface 250 defines a smooth, continuous conical shape. Radially inboard locking member 210 includes radially inboard locking surface 220 which defines a corresponding smooth, continuous conical shape. Locking mechanism 200 includes an actuator sleeve 44 with a wider diameter at the proximal end and a radially smaller segment 212 which defines radially inboard locking member 210.

FIGS. 26A, 26B, 26C, 26D and 26E diagrammatically illustrate various configurations and shapes of locking mechanism 200. In FIG. 26A, locking member 210 includes a radially inboard locking surface with two separate radially inboard faces 220a, 220b. Second locking member 240 includes radially outboard locking surfaces with radially inboard faces 250a, 250b. First locking member 210 defines two inward-facing bowls and second locking member 240 defines two facing frustoconical shapes with a gap between the two. In FIG. 26B, locking members 210 and 240 are reversed such that locking member 210 defines two outward-facing bowls with a gap between the two, and locking member 240 defines two opposing frustoconical shapes with a gap between the two. In FIG. 26C, locking member 210 defines two facing bowls, and locking member 240 defines two facing frustoconical shapes. In FIG. 26D, locking member 210 defines two outward-facing bowls, and locking member 240 defines two tear-drop shapes. In FIG. 26E, locking member 210 defines two outward-facing bowls, and locking member 240 defines two opposing frustoconical shapes.

FIGS. 27A, 27B and 27C diagrammatically illustrate deployment system 70 with expandable frame 10 in three different states and with locking mechanism 200 in corresponding states. In FIG. 27A, expandable frame 10 is in a fully open position, and corresponding locking mechanism 200 shows radially inboard locking surface 220a substantially contiguous to radially outboard locking surface 250a, thus establishing a friction lock. In FIG. 27B, expandable frame 10 is in a partially deployed state. The inboard locking surfaces 220a, 220b are not in contact with outboard locking surfaces 250a, 250b. In FIG. 27C, expandable frame 10 is in a fully closed state. Radially inboard locking surface 220b is substantially contiguous to radially outboard locking surface 250b, establishing a lock thereat.

FIG. 28 diagrammatically illustrates actuator sleeve 44 and expandable frame 10 placed over or run over the proximal end of guide wire 12. Expandable frame 10 is in a radially closed form.

FIG. 29 diagrammatically illustrates deployment system 70 with a detachably coupled locking mechanism 200 with an extender actuator sleeve segment. Locking mechanism 200 includes a tactile responsive interface 270. Interface 270 may also include visual indicators. See FIGS. 18B and 20. FIG. 29 includes a two-part guide wire 12 with a coupling 274, 276. Coupling 274, 276 has a threaded interface. The coupling could also be a detent-type coupling. Actuator sleeve 44 is also a detachably coupled two-part actuator. Actuator sleeve 44 has a threaded interface coupling 278, 280 or a detent-lock. In FIG. 29, the proximal end of guide wire 12 and actuation sleeve 44 are separated from the distal counterparts. Expandable frame 10 in a radially closed state.

FIG. 30 diagrammatically illustrates deployment system 70 with a partially detachably coupled locking mechanism 200 in a decoupled state. Expandable frame 10 is locked in a slightly radially deployed state by the locking of guide wire 12 and actuation sleeve 44 at the distal end of locking mechanism 200. Locking members 210 and 240 are substantially contiguous thereby creating the friction lock between guide wire 12 and actuation sleeve 44 when frame 10 is fully open (not shown).

FIG. 31 diagrammatically illustrates the distal end of deployment system 70 with the actuator sleeve 44 and expandable frame 10 partially slid over the guide wire 12. Expandable frame 10 is in radially closed form with frame end 40 not in contact with distal stop 16. Radially inboard locking member 240 is not in contact with radially outboard locking member 210.

The operation of the friction locking mechanism follows. Locking mechanism 200 locks expandable frame 10 in a radially open (deployed) state or in a radially closed state. Locking mechanism 200 may include one friction locking interface as shown in FIGS. 21A, 21B, 22, 24, 25A and 25B, or may include dual or forward and aft friction locking interfaces as shown in FIGS. 26A through 26E, 27A through 27C, 29, 30 and 31, thus giving the locking mechanism capability of locking the expandable frame in both a radially open form and in a closed form.

FIG. 22 illustrates a locking mechanism used to lock expandable frame 10 in a radially deployed state. Although guide wire 12 and actuation sleeve 44 can be moved longitudinally with respect to each other, it will be assumed for purposes of describing the operation of the locking mechanism that guide wire 12 is stationary. In FIG. 22, the user pushes actuation sleeve 44 in a distal direction as indicated by arrow D. This longitudinally distal movement of actuation sleeve 44 relative to guide wire 12 causes the expandable frame to move distally over the guide wire until distal or fore frame collar 40 abuts distal stop 16 (see FIG. 25B). Distal stop 16 limits further distal movement of distal frame collar 40 along guide wire 12. As the actuation sleeve 44 is pushed further, proximal or aft frame collar 46 continues to move distally causing the frame struts 21 and 25 to radially deploy (see FIG. 25B). Thus, as expandable frame 10 opens, it attains an open, radially expanded, longitudinally foreshortened form.

Locking mechanism 200 also engages during the aforementioned longitudinally distal movement of actuation sleeve 44 relative to guide wire 12. As actuation sleeve 44 is moved distally, radially inboard locking surface 220 comes in contact with radially outboard locking surface 250. As the two locking surfaces become substantially contiguous, the surfaces establish a friction locking interface such that actuation sleeve 44 is immobile with respect to the guide wire 12. The slope of the radially inboard friction face defined by locking surface 220 and the slope of the radially outboard friction face defined by locking surface 250 determine the duration or displacement of the friction locking interface established between the two locking surfaces. The more gradual the slope the longer the friction locking interface and, thus, the greater the longitudinal displacement of actuation sleeve 44. Upon radially opening expandable frame 10 to a predetermined diameter, the actuation sleeve 44 and the guide wire 12 are locked together by the friction locking interface of locking mechanism 200. In order to unlock the locking mechanism, the user pulls on actuation sleeve 44 in a direction opposite arrow D such that the lock established by the friction locking interface no longer holds the actuation sleeve 44 immobile relative to the guide wire 12.

FIG. 24 illustrates a locking mechanism used to lock expandable frame 10 in a radially closed state. It will be assumed for purposes of the foregoing that expandable frame has been deployed and the distal or fore end 40 of expandable frame 10 is temporarily retained as described in connection with FIGS. 10 through 12, above. In FIG. 24, the user pulls actuation sleeve 44 in a proximal direction as indicated by arrow P. This longitudinally proximal movement of actuation sleeve 44 relative to guide wire 12 causes the proximal frame end to move proximally over the guide wire 12 such that the frame struts move radially inboard toward the guide wire (see FIG. 25A). The proximal movement of actuation sleeve 44 causes the frame struts to bend toward their approximate original shape until the longitudinal tension overcomes the temporary retaining force of the temporary latch at distal stop 16. Thus, as expandable frame 10 closes, it attains a closed, radially compact, elongated form.

Locking mechanism 200 also engages during the aforementioned longitudinally proximal movement of actuation sleeve 44 relative to guide wire 12. In FIG. 24, as actuation sleeve 44 is moved proximally, radially inboard locking surface 220 comes in contact with radially outboard locking surface 250. As the two locking surfaces become substantially contiguous, the surfaces establish a friction locking interface such that actuation sleeve 44 is immobile with respect to the guide wire 12. Similarly, the slope of the radially inboard friction face defined by locking surface 220 and the slope of the radially outboard friction face defined by locking surface 250 determine the duration or displacement of the friction locking interface established between the two locking surfaces. The more gradual the slope the longer the friction locking interface and, thus, the greater the longitudinal displacement of actuation sleeve 44. Upon radially closing expandable frame 10 to a predetermined diameter, the actuation sleeve 44 and the guide wire 12 are locked together by the friction locking interface of locking mechanism 200. In order to unlock the locking mechanism, the user pushes on actuation sleeve 44 in a direction opposite arrow P such that the lock established by the friction locking interface no longer holds the actuation sleeve 44 immobile relative to the guide wire 12.

FIG. 21B diagrammatically illustrates an alternative locking interface to lock expandable frame 10 in a radially deployed state. In FIG. 21B, radially inboard friction face 220 defines cavities 228 which interact with protrusions 258 on radially outboard friction face 250 during radial deployment of expandable frame 10. As the two friction faces come in contact with each other one or more of protrusions 258 align with one or more corresponding cavities 228, thus creating a locking interface with steps in addition to the friction locking interface (alternatively, radially inboard face 220 can define the protrusions and radially outboard face 250 can define the cavities). Additionally, a combination in which both faces define protrusions can also be utilized. Finally, the aforementioned locking faces may also be utilized to lock expandable frame 10 in a radially closed state.

The locking mechanism 200 discussed above in connection with FIGS. 22 and 24 can be combined to form a locking mechanism that is capable of locking the expandable frame in both a radially expanded form and a radially closed form. FIGS. 27A, 27B and 27C illustrate a locking mechanism 200 capable of locking expandable frame 10 during radially deployment and radial closure. In FIG. 27A, actuation sleeve 44 has been longitudinally moved in a distal direction such that expandable frame 10 is in a radially deployed state and radially inboard locking surface 220a and radially outboard locking surface 250a are substantially contiguous creating a friction locking interface such that actuation sleeve 44 is immobile or locked in position relative to guide wire 12. In FIG. 27A, locking mechanism 200 is disengaged. Radially inboard locking surfaces 220a, 220b are not in contact with corresponding radially outboard locking surfaces 250a, 250B. Expandable frame 10 is in transition between deployment and closure. In FIG. 27C, actuation sleeve 44 has been longitudinally moved in a proximal direction such that expandable frame 10 is in a radially closed form and radially inboard locking surface 220b and radially outboard locking surface 250b are substantially contiguous creating a friction locking interface such that actuation sleeve 44 is immobile or locked in position relative to guide wire 12.

As previously discussed in connection with the filter device, there are circumstances in which a physician may need to lock the expandable frame (with or without the filter) in order to perform other surgical or medical techniques. During such techniques, it may be convenient or necessary to remove the locking mechanism 200 from the proximal end of deployment system 70 in order to position other instruments or catheters over guide wire 12 and actuation sleeve 44. FIGS. 28, 29, 30 and 31 diagrammatically illustrate a deployment system 70 with a detachable locking mechanism 200. In FIG. 29, when locking mechanism 200 is detached, actuation sleeve 44 and expandable frame 10 are free to move longitudinally and radially with respect to guide wire 12 (except beyond distal stop 16).

In FIGS. 29 and 31, actuation sleeve 44 and guide wire 12 include coupling interfaces which permit the physician to lock the expandable frame 10 in a radially open or deployed state prior to and after removal of the proximal end of locking mechanism 200. FIG. 31 illustrates the distal end of locking mechanism 200 and deployment system 70 prior to deployment of expandable frame 10. In FIG. 30, actuation sleeve 44 has been longitudinally moved in a distal direction relative to guide wire 12 such that expandable frame 10 is radially deployed and radially inboard locking member 240 has engaged radially outboard locking member 210 establishing a friction locking interface.

As discussed earlier in connection with the filter device, it is important that the physician performing surgical techniques utilizing the locking mechanism be visually and tactually notified when expandable frame 10 is approaching distal stop 16 and when the expandable frame is in a radially open or closed state. In order to provide such notification, locking mechanism 200 in FIGS. 29 and 30 utilizes several visual, tactile indicators 270. The indicators may also be utilized as temporary stops or latch points 116, 117, 118, 119. Again, only a single temporary stop or latch point 116 may be utilized in connection with the present invention.

The frame deployment system 70 may be utilized in a number of medical procedures such as deployment of a blood filter (see FIG. 1, for example) or deployment of a frame (see FIG. 8A, for example). The frame with a filter may be utilized in vascular, urologic and other catheterization procedures. Hence the friction lock can be used in a controllable deployment system.

The claims appended hereto are meant to cover modifications and changes within the scope and spirit of the present invention.

What is claimed is:

1. A filter device for capturing embolic material in a blood vessel comprising:
    a guide wire having a proximal end and a distal end;
    an expandable frame of frame members having a radiopaque coating and having a closed, radially compact form and an open, radially expanded form and a fore end and an aft end, said aft end coupled to said distal end of said guide wire, said frame of frame members in said radially expanded form forming a pair of facing generally frustoconical frame structures;
    a filter material attached to one of said pair of frustoconical frame structures; and
    an actuator sleeve with a proximal end and a distal end adapted to run over said guide wire, said actuator sleeve enabling longitudinal compression of said expandable frame and frame members thereby causing said frame to radially expand and deploy said filter material; and
    one of a sleeve and guide wire lock at said proximal end of said actuator sleeve or a frame and guide wire lock at said fore end.

2. A filter device as claimed in claim 1 wherein said radiopaque coating is one of gold or platinum.

3. A filter device for capturing embolic material in a blood vessel comprising:
    a guide wire having a proximal end and a distal end;
    an expandable frame of frame members having a closed, radially compact form and an open, radially expanded form and a fore end and an aft end, said fore end coupled to said distal end of said guide wire, said frame of frame members in said radially expanded form forming a pair of facing generally frustoconical frame structures;
    a filter material attached to one of said pair of frustoconical frame structures; and
    an actuator sleeve adapted to run over said guide wire, said actuator sleeve having a flexible distal end as a strain relief segment coupled to said aft end of said expandable frame, enabling longitudinal compression of said expandable frame and frame members thereby causing said frame to radially expand and deploy said filter material.

4. A filter device as claimed in claim 3 wherein said flexible distal end is a coiled material.

5. A filter device as claimed in claim 4 wherein said flexible distal end permits flexation of the frame relative to the guide wire in excess of 90 degrees.

6. A controllable deployment system for a radially expandable frame utilized during catheterization comprising:
    a guide wire having a proximal end and a distal end;
    a radially expandable radiopaque frame having a plurality of struts with a closed, radially compact, elongated form and an open, radially expanded, longitudinally foreshortened form, said radiopaque frame having distal and proximal frame ends;
    said guide wire extending through said expandable radiopaque frame;
    an elongated actuation sleeve having a distal end, a proximal end, and a lumen through which passes said guide wire, said distal sleeve end coupled to said proximal frame end; and
    one of a sleeve and guide wire lock at said proximal end of said actuation sleeve or a frame and guide wire lock at said distal frame end.

7. A system as claimed in claim 6 wherein said radiopaque frame is coated with one of gold or platinum.

8. A controllable deployment system for a radially expandable frame utilized during catheterization comprising:
    a guide wire having a proximal end and a distal end;
    a radially expandable frame having a closed, radially compact, elongated form and an open, radially expanded, longitudinally foreshortened form, said frame having distal and proximal frame ends;
    said guide wire extending through said expandable frame; and
    an elongated actuation sleeve having a distal flexible end as a coiled strain relief segment, a proximal end, and a lumen through which passes said guide wire, said distal flexible end coupled to said proximal frame end.

9. A system as claimed in claim 8 wherein said distal flexible end permits flexation of the frame relative to the guide wire in excess of 90 degrees.

10. A system as claimed in claim 8 wherein said frame is radiopaque.

11. A filter device for capturing embolic material in a blood vessel comprising:

a guide wire having a proximal end and a distal end;

an expandable frame of frame members having a radiopaque coating and having a closed, radially compact form and an open, radially expanded form and a fore end and an aft end, said aft end coupled to said distal end of said guide wire, said frame of frame members in said radially expanded form forming a pair of facing generally frustoconical frame structures;

a filter material attached to one of said pair of frustoconical frame structures; and an actuator sleeve with a proximal end and a distal end adapted to run over said guide wire, said actuator sleeve enabling longitudinal compression of said expandable frame and frame members thereby causing said frame to radially expand and deploy said filter material; and one of a sleeve and guide wire lock at said proximal end of said actuator sleeve or a frame and guide wire lock at said fore end.

* * * * *